(12) United States Patent
Saitoh et al.

(10) Patent No.: US 7,709,104 B2
(45) Date of Patent: May 4, 2010

(54) AMINOANTHRYL DERIVATIVE-SUBSTITUTED PYRENE COMPOUND AND ORGANIC LIGHT-EMITTING DEVICE

(75) Inventors: Akihito Saitoh, Yokohama (JP); Keiji Okinaka, Kawasaki (JP); Naoki Yamada, Tokyo (JP); Masataka Yashima, Tokyo (JP); Akihiro Senoo, Kawasaki (JP); Kazunori Ueno, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 477 days.

(21) Appl. No.: 11/280,311

(22) Filed: Nov. 17, 2005

(65) Prior Publication Data
US 2006/0115678 A1 Jun. 1, 2006

(30) Foreign Application Priority Data
Nov. 26, 2004 (JP) .............................. 2004-342463
Sep. 21, 2005 (JP) .............................. 2005-273622

(51) Int. Cl.
H01L 51/54 (2006.01)
C09K 11/06 (2006.01)

(52) U.S. Cl. ........................ 428/690; 428/917; 313/504; 313/506; 564/427; 585/26; 252/301.16; 257/40; 257/E51.049; 257/E51.051

(58) Field of Classification Search ................. 428/690, 428/917; 313/502–509; 585/24–27; 564/426–427, 564/431, 433–434, 308
See application file for complete search history.

(56) References Cited

U.S. PATENT DOCUMENTS

| 4,539,507 | A | 9/1985 | VanSlyke et al. | ............. | 313/504 |
| 4,720,432 | A | 1/1988 | VanSlyke et al. | ............. | 428/457 |
| 4,885,211 | A | 12/1989 | Tang et al. | ............. | 428/457 |
| 5,130,603 | A | 7/1992 | Tokailin et al. | ............. | 313/504 |
| 5,151,629 | A | 9/1992 | VanSlyke | ............. | 313/504 |
| 5,227,252 | A | 7/1993 | Murayama et al. | ............. | 428/690 |
| 5,247,190 | A | 9/1993 | Friend et al. | ............. | 257/40 |
| 5,317,169 | A | 5/1994 | Nakano et al. | ............. | 257/40 |
| 5,382,477 | A | 1/1995 | Saito et al. | ............. | 428/690 |
| 5,409,783 | A | 4/1995 | Tang et al. | ............. | 428/690 |
| 5,514,878 | A | 5/1996 | Holmes et al. | ............. | 257/40 |
| 5,635,308 | A | 6/1997 | Inoue et al. | ............. | 428/690 |
| 5,672,678 | A | 9/1997 | Holmes et al. | ............. | 528/373 |
| 5,726,457 | A | 3/1998 | Nakano et al. | ............. | 257/40 |
| 5,759,444 | A | 6/1998 | Enokida et al. | ........ | 252/301.16 |
| 6,093,864 | A | 7/2000 | Tokailin et al. | ............. | 585/25 |
| 6,251,531 | B1 | 6/2001 | Enokida et al. | ............. | 428/690 |
| 6,406,801 | B1 | 6/2002 | Tokito et al. | ............. | 428/690 |
| 6,579,630 | B2 * | 6/2003 | Li et al. | ............. | 428/690 |
| 6,713,192 | B2 | 3/2004 | Fukuoka et al. | ............. | 428/690 |
| 7,129,386 | B2 | 10/2006 | Saitoh et al. | ............. | 585/26 |
| 2002/0048688 | A1 | 4/2002 | Fukuoka et al. | ............. | 428/690 |
| 2004/0263067 | A1 | 12/2004 | Saitoh et al. | ............. | 313/504 |
| 2004/0265632 | A1 | 12/2004 | Okinaka et al. | ............. | 428/690 |
| 2006/0113528 | A1 | 6/2006 | Okinaka et al. | ............. | 257/40 |
| 2006/0121312 | A1 | 6/2006 | Yamada et al. | ............. | 428/690 |
| 2006/0125378 | A1 | 6/2006 | Saitoh et al. | ............. | 313/504 |

FOREIGN PATENT DOCUMENTS

| JP | 02-247278 | | 10/1990 |
| JP | 03-255190 | | 11/1991 |
| JP | 04-145192 | | 5/1992 |
| JP | 05-202356 | | 8/1993 |
| JP | 05-247460 | | 9/1993 |
| JP | 08-012600 | | 1/1996 |
| JP | 09-157643 | | 6/1997 |
| JP | 09-202878 | | 8/1997 |
| JP | 09-227576 | | 9/1997 |
| JP | 10-072579 | | 3/1998 |
| JP | 11-008068 | | 1/1999 |
| JP | 3008897 | | 12/1999 |
| JP | 2001-284050 | | 10/2001 |
| JP | 2002063988 | * | 2/2002 |
| JP | 2002-324678 | | 11/2002 |
| JP | 2003313156 A | * | 11/2003 |
| JP | 2005206551 | * | 8/2005 |
| WO | WO 2004020388 | * | 3/2004 |

OTHER PUBLICATIONS

Machine Translation of JP 2005206551.*
Machine Translation of JP 2002063988.*
Machine translation of JP 2003313156. (Nov. 2003).*

(Continued)

*Primary Examiner*—D. Lawrence Tarazano
*Assistant Examiner*—Michael Wilson
(74) *Attorney, Agent, or Firm*—Fitzpatrick, Cella, Harper & Scinto

(57) ABSTRACT

There is provided an aminoanthryl derivative-substituted pyrene compound represented by the following general formula (1).

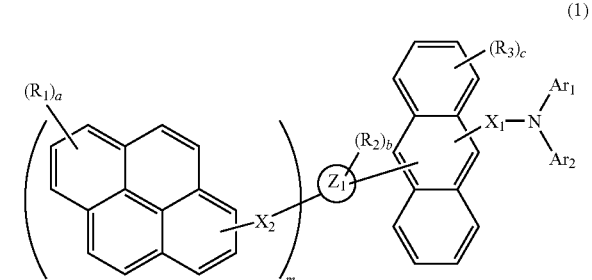

The compound is useful as a compound for an organic light-emitting device exhibiting highly pure luminescent color, and an optical output with high efficiency, high luminance, and long life.

4 Claims, 2 Drawing Sheets

OTHER PUBLICATIONS

Betzig et al., "Collection Mode Near-field Scanning Optical Microscopy," *Appl. Phys. Lett.*, vol. 51, No. 25, 2088-2091 (1987).

Burroughes et al., "Light-emitting Diodes Based on Conjugated Polymers," *Nature*, vol. 347, 539-541 (1990).

Baldo et al., "Very High-efficiency Green Organic Light-emitting Devices Based on Electrophosphorescence," *Appl. Phys. Lett.*, vol. 75, No. 1, 4-6 (1999).

* cited by examiner

AMINOANTHRYL DERIVATIVE-SUBSTITUTED PYRENE COMPOUND AND ORGANIC LIGHT-EMITTING DEVICE

BACKGROUND OF THE INVENTION

1. Field of the Invention

The present invention relates to an aminoanthryl derivative-substituted pyrene compound, and to an organic light-emitting device using the compound.

2. Related Background Art

An organic light-emitting device is a device which includes a thin film containing a fluorescent organic compound between an anode and a cathode, which generates an exciton from the fluorescent compound by injection of an electron and an electron hole (hole) from each electrode, and which utilizes light to be radiated when the exciton returns to a ground state.

In a study conducted by Eastman Kodak Company in 1987 (Appl. Phys. Lett., 51, 913 (1987)), an anode formed of ITO, a cathode formed of a magnesium-silver alloy, and an electron transport material and a light-emitting material each formed of an aluminum quinolinol complex are used. Further, there is reported light emission of about 1,000 cd/m$^2$ under application of a voltage of about 10 V from a device having a function-separated two-layer structure using a triphenylamine derivative as a hole transport material. Related patent documents include U.S. Pat. No. 4,539,507, U.S. Pat. No. 4,720,432, and U.S. Pat. No. 4,885,211.

Further, light emission in ultraviolet to infrared regions is possible by changing the type of fluorescent organic compound. Recently, various compounds have been studied actively (U.S. Pat. No. 5,151,629, U.S. Pat. No. 5,409,783, U.S. Pat. No. 5,382,477, Japanese Patent Application Laid-Open No. H02-247278, Japanese Patent Application Laid-Open No. H03-255190, Japanese Patent Application Laid-Open No. H05-202356, Japanese Patent Application Laid-Open No. H09-202878, and Japanese Patent Application Laid-Open No. H09-227576).

In addition to the organic light-emitting device using a low molecular weight material as described above, an organic light-emitting device using a conjugated polymer has been reported by a group of Cambridge University (Nature, 347, 539 (1990)). In this report, light emission has been confirmed from a single layer of polyphenylene vinylene (PPV) formed in a coating system. Patents related to an organic light-emitting device using a conjugated polymer include U.S. Pat. No. 5,247,190, U.S. Pat. No. 5,514,878, U.S. Pat. No. 5,672,678, Japanese Patent Application Laid-Open No. H04-145192, and Japanese Patent Application Laid-Open No. H05-247460.

Recently, an organic phosphorescence device using an iridium complex such as Ir(ppy)$_3$ as a light-emitting material has attracted attention and its high luminous efficiency has been reported (Appl. Phys. Lett., 75, 4 (1999)).

Recent advances in organic light-emitting device are remarkable and characteristics of the organic light-emitting device allow formation of a thin and lightweight light-emitting device with high luminance under application of a low voltage, wide range of emission wavelengths, and high-speed response, thereby suggesting the possibility of extensive uses. However, the organic light-emitting device still has many problems in durability such as change over long-term use, and degradation by an atmospheric gas containing oxygen, by moisture, and the like. For application of the organic light-emitting device to a full-color display or the like, blue, green, and red light emissions with extended-life, high conversion efficiency, and high color purity are required under the present circumstances, and various proposals have been made.

An example of a material containing an anthracene ring used for an organic light-emitting device is a phenylanthracene derivative disclosed in Japanese Patent Application Laid-Open No. H08-012600. In particular, use of a phenylanthracene derivative as a blue light-emitting material or an electron-injection transporting material allows formation of a favorable organic film because of low crystallinity of the phenylanthracene derivative. However, the phenylanthracene derivative has insufficient luminous efficiency and durable life for practical use.

Japanese Patent Application Laid-Open No. H09-157643 and Japanese Patent Application Laid-Open No. H10-072579 disclose an aminoanthracene derivative and a diaminoanthracene derivative, respectively. Those materials are used as light-emitting materials and allow green light emission. However, devices produced by using those materials each have low luminous efficiency and insufficient durable life for practical use.

Japanese Patent No. 3008897 discloses a device using a specific bianthryl compound as a light-emitting material, which allows light emission with high luminance. However, the patent document includes no description of luminous efficiency or durable life.

Japanese Patent Application Laid-Open No. H11-008068 discloses a device using a specific anthracene compound containing an olefin site as a light-emitting material, which allows yellow to red light emissions. However, the device has insufficient luminous efficiency for practical use.

Japanese Patent Application Laid-Open No. 2001-284050 discloses a device containing an anthracene derivative with a specific structure, an electron transport compound, and another fluorescent compound in a light-emitting medium layer, to thereby provide a red light-emitting device with improved reliability. However, the device has insufficient luminous efficiency for practical use, and blue light emission is hardly observed because of a device structure.

Japanese Patent Application Laid-Open No. 2002-324678 discloses an example of a material containing pyrene substituted into a benzene ring used for an organic light-emitting device, to thereby provide a device with favorable luminous properties and durability. However, the device has low external quantum efficiency, and the patent document includes no specific description of durable life.

SUMMARY OF THE INVENTION

The present invention has been made in view of solving problems in conventional art, and an object of the present invention is therefore to provide a compound for an organic light-emitting device exhibiting highly pure luminescent color, and an optical output with high efficiency, high luminance, and long life. Another object of the present invention is to provide an organic light-emitting device which can be produced easily and at relatively low cost.

The inventors of the present invention have conducted extensive studies for attaining the above-mentioned objects, and have completed the present invention.

That is, according to one aspect of the present invention, there is provided an aminoanthryl derivative-substituted pyrene compound represented by the following general formula (1):

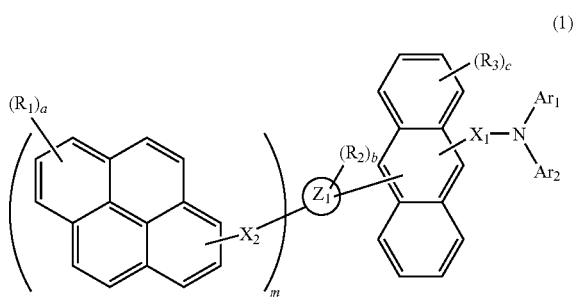

(1)

(in the general formula (1): $Ar_1$ and $Ar_2$ each represent a group selected from the group consisting of a substituted or unsubstituted aryl group and a substituted or unsubstituted heterocyclic group; $Ar_1$ and $Ar_2$ may each represent a group bonded through a linking group; $Ar_1$ and $Ar_2$ may be identical to or different from each other; $Ar_1$ and $Ar_2$ may be bonded to each other to form a ring;

$Z_1$ represents a group selected from the group consisting of a direct single bond, a substituted or unsubstituted alkylene group, a substituted or unsubstituted alkenylene group, a substituted or unsubstituted alkynylene group, a substituted or unsubstituted aralkylene group, a substituted or unsubstituted arylene group, and a substituted or unsubstituted divalent heterocyclic group; $Z_1$ may represent a group bonded through a linking group;

$X_1$ represents a group selected from the group consisting of a direct single bond, a substituted or unsubstituted arylene group, and a substituted or unsubstituted divalent heterocyclic group; $X_1$ may represent a group bonded through a linking group;

$X_2$ represents a group selected from the group consisting of a direct single bond, a substituted or unsubstituted alkylene group, a substituted or unsubstituted alkenylene group, a substituted or unsubstituted alkynylene group, a substituted or unsubstituted aralkylene group, a substituted or unsubstituted arylene group, and a substituted or unsubstituted divalent heterocyclic group; $X_2$ may represent a group bonded through a linking group;

$R_1$ and $R_3$ each represent a group selected from the group consisting of a hydrogen atom, a deuterium atom, a halogen atom, a substituted or unsubstituted alkyl group, a substituted or unsubstituted aryl group, a substituted or unsubstituted alkoxy group, and a substituted or unsubstituted amino group; $R_1$ and $R_3$ may be identical to or different from each other;

$R_2$ represents a group selected from the group consisting of a hydrogen atom, a deuterium atom, a halogen atom, a substituted or unsubstituted alkyl group, a substituted or unsubstituted aralkyl group, a substituted or unsubstituted alkenyl group, a substituted or unsubstituted alkynyl group, a substituted or unsubstituted alkoxy group, a substituted or unsubstituted sulfide group, a substituted or unsubstituted amino group, a substituted or unsubstituted aryl group, and a substituted or unsubstituted heterocyclic group; and $R_2$ may be identical to or different from each other when b is in plural; and a represents an integer of 1 to 9; b represents an integer of 1 to 4; c represents an integer of 1 to 8; m represents an integer of 1 to 3).

According to another aspect of the present invention, there is provided an organic light-emitting device including: a pair of electrodes consisting of an anode and a cathode in which at least one electrode is transparent or translucent; and a layer or a plurality of layers each containing an organic compound and held between the pair of electrodes, in which at least one of the layers each containing an organic compound contains at least one aminoanthryl derivative-substituted pyrene compound.

The aminoanthryl derivative-substituted pyrene compound of the present invention is a material for an organic light-emitting device having multifunctional properties such as highly efficient light emission and efficient electron and hole transport in a molecule. The organic light-emitting device using the pyrene compound of the present invention allows highly efficient light emission under application of a low voltage. Further, change in substituent of the pyrene compound can easily provide various luminescent colors and excellent durability.

DESCRIPTION OF THE PREFERRED EMBODIMENTS

Figure 1:
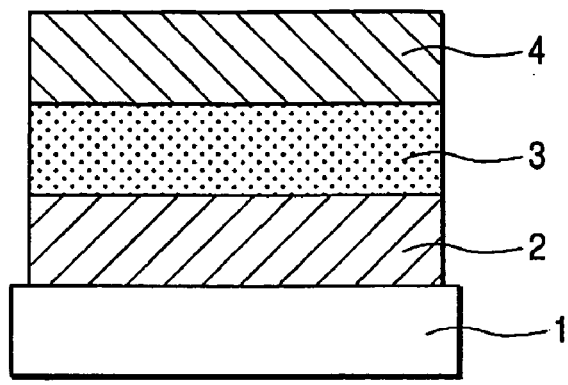
FIG. 1 is a sectional view showing an example of an organic light-emitting device according to the present invention.

Hereinafter, the present invention will be described more specifically.

First, description will be given of an aminoanthryl derivative-substituted pyrene compound of the present invention.

The pyrene compound of the present invention can be used mainly as a material for an organic light-emitting device. The compound may be used for a light emission layer and used alone in the light emission layer or used in a dopant (guest) material or a host material, to thereby provide a device with high color purity, high luminous efficiency, and long life.

For the pyrene compound of the present invention, molecular design was performed for arranging an aminoanthryl derivative and a pyrene derivative in consideration of providing multifunctional properties such as highly efficient light emission and efficient electron and hole transport in a molecule. For introduction of a substituted amino group into an anthryl group for highly efficient light emission and hole transport property, a HOMO/LUMO level of a material may be adjusted by changing a substituent on the amino group, to thereby change a luminescent color to luminescent colors of blue, green light emission, and other colors at longer wavelengths. Molecular design may be performed easily through prediction of a HOMO/LUMO level by calculation in consideration of difference in energy levels among a host material, a hole transport layer, and an electron transport layer. The pyrene derivative is most preferably substituted at a 1- or 4-position through synthesis and shows high quantum efficiency. Further, improvement in carrier transport property can be expected because of overlapping pyrene rings. In addition, the introduction of the amino group on the anthryl group may increase Tg, to thereby provide a material with favorable thermal stability. Further, introduction of a bulky substituent typified by a tert-butyl group into a pyrene ring and a phenyl group on an amine allows suppression of cohesion between molecules while appropriate carrier transport property is maintained, to thereby improve the life of the device. In addition to the above-mentioned consideration, the pyrene compound of the present invention is designed in consideration of suppressing molecular vibration by an isotope effect to suppress thermal inactivation and has a deuterium atom-containing molecule unit introduced thereinto. The pyrene compound of the present invention is obtained through molecular design based on the consideration described above, and the present invention has been completed.

For use of the pyrene compound of the present invention as a dopant material, a concentration of the dopant with respect to a host material is 0.01 wt % to 80 wt %, and preferably 1 wt % to 40 wt %. The dopant material may be included in an entire layer formed of the host material uniformly or with a concentration gradient, or may be partly included in a certain region of the layer of the host material having a region containing no dopant material.

Examples of a substituted or unsubstituted alkyl group in the general formula (1) include, but are not limited to: a methyl group; a methyl-d1 group; a methyl-d3 group; an ethyl group; an ethyl-d5 group; an n-propyl group; an n-butyl group; an n-pentyl group; an n-hexyl group; an n-heptyl group; an n-octyl group; an n-decyl group; an iso-propyl group; an iso-propyl-d7 group; an iso-butyl group; a sec-butyl group; a tert-butyl group; a tert-butyl-d9 group; an iso-pentyl group; a neopentyl group; a tert-octyl group; a fluoromethyl group; a difluoromethyl group; a trifluoromethyl group; a 2-fluoroethyl group; a 2,2,2-trifluoroethyl group; a perfluoroethyl group; a 3-fluoropropyl group; a perfluoropropyl group; a 4-fluorobutyl group; a perfluorobutyl group; a 5-fluoropentyl group; a 6-fluorohexyl group; a chloromethyl group; a trichloromethyl group; 2-chloroethyl group; a 2,2,2-trichloroethyl group; a 4-chlorobutyl group; a 5-chloropentyl group; a 6-chlorohexyl group; a bromomethyl group; a 2-bromoethyl group; an iodomethyl group; a 2-iodoethyl group; a hydroxymethyl group; a hydroxyethyl group; a cyclopropyl group; a cyclobutyl group; a cyclopentyl group; a cyclohexyl group; a cyclopentylmethyl group; a cyclohexylmethyl group; a cyclohexylethyl group; a 4-fluorocyclohexyl group; a norbornyl group; and an adamantyl group.

Examples of a substituted or unsubstituted aralkyl group include, but are not limited to: a benzyl group; a 2-phenylethyl group; a 2-phenylisopropyl group; a 1-naphthylmethyl group; a 2-naphthylmethyl group; a 2-(1-napthyl)ethyl group; a 2-(2-napthyl)ethyl group; a 9-anthrylmethyl group; a 2-(9-anthryl)ethyl group; a 2-fluorobenzyl group; a 3-fluorobenzyl group; a 4-fluorobenzyl group; a 2-chlorobenzyl group; a 3-chlorobenzyl group; a 4-chlorobenzyl group; a 2-bromobenzyl group; a 3-bromobenzyl group; and a 4-bromobenzyl group.

Examples of a substituted or unsubstituted alkenyl group include, but are not limited to: a vinyl group; an allyl group (a 2-propenyl group); a 1-propenyl group; an iso-propenyl group; a 1-butenyl group; a 2-butenyl group; a 3-butenyl group; and a styryl group.

Examples of a substituted or unsubstituted alkynyl group include, but are not limited to: an acetylenyl group; a phenylacetylenyl group; and a 1-propynyl group.

Examples of a substituted or unsubstituted aryl group include, but are not limited to: a phenyl group; a phenyl-d5 group; a 4-methylphenyl group; a 4-methoxyphenyl group; a 4-ethylphenyl group; a 4-fluorophenyl group; a 4-trifluorophenyl group; a 3,5-dimethylphenyl group; a 2,6-diethylphenyl group; a mesityl group; a 4-tert-butylphenyl group; a ditolylaminophenyl group; a biphenyl group; a terphenyl group; a naphthyl group; a naphthyl-d7 group; an acenaphthylenyl group; an anthryl group; an anthryl-d9 group; a phenanthryl group; a phenanthryl-d9 group; a pyrenyl group; a pyrenyl-d9 group; an acephenanthrylenyl group; an aceanthrylenyl group; a chrysenyl group; a dibenzo chrysenyl group; a benzoanthryl group; a benzoanthryl-d11 group; a dibenzoanthryl group; a naphthacenyl group; a picenyl group; a pentacenyl group; a fluorenyl group; a triphenylenyl group; a perylenyl group; and a perylenyl-d11 group.

Examples of a substituted or unsubstituted heterocyclic group include, but are not limited to: a pyrrolyl group; a pyridyl group; a pyridyl-d5 group; a bipyridyl group; a methylpyridyl group; a pyrimidinyl group; a pyrazinyl group; a pyridazinyl group; a terpyrrolyl group; a thienyl group; a thienyl-d4 group; a terthienyl group; a propylthienyl group; a benzothienyl group; a dibenzothienyl group; a dibenzothienyl-d7 group; a furyl group; a furyl-d4 group; a benzofuryl group; an isobenzofuryl group; dibenzofuryl group; a dibenzofuryl-d7 group; a quinolyl group; a quinolyl-d6 group; an isoquinolyl group; a quinoxalinyl group; a naphthylidinyl group; a quinazolinyl group; a phenanthridinyl group; an indolizinyl group; a phenazinyl group; a carbazolyl group; an oxazolyl group; an oxadiazolyl group; a thiazolyl group; a thiadiazolyl group; an acridinyl group; and a phenazinyl group.

Examples of a substituted or unsubstituted aralkylene group include, but are not limited to: a benzylene group; a 2-phenylethylene group; a 2-phenylisopropylene group; a 1-naphthylmethylene group; a 2-naphthylmethylene group; a 9-anthrylmethylene group; a 2-fluorobenzylene group; a 3-fluorobenzylene group; a 4-fluorobenzylene group; a 4-chlorobenzylene group; and a 4-bromobenzylene group.

Examples of a substituted or unsubstituted alkenylene group include, but are not limited to: a vinylene group; an iso-propenylene group; a styrylene group; and a 1,2-diphenylvinylene group.

Examples of a substituted or unsubstituted alkynylene group include, but are not limited to, an acetylenylene group and a phenyl acetylenylene group.

Examples of a substituted or unsubstituted arylene group include, but are not limited to: a phenylene group; a biphenylene group; a tetrafluorophenylene group; a dimethylphenylene group; a naphthylene group; a phenanthrylene group; a pyrenylene group; a tetracenylene group; a pentacenylene group; and a perylenylene group.

Examples of a substituted or unsubstituted divalent heterocyclic group include, but are not limited to: a furylene group; a pyrrolylene group; a pyridylene group; a terpyridylene group; a thienylene group; a terthienylene group; an oxazolylene group; a thiazolylene group; and a carbazolylene group.

In a substituted or unsubstituted amino (—NR'R") group, examples of R' and R" include, but are not limited to: a hydrogen atom; a deuterium atom; the above-mentioned substituted or unsubstituted alkyl group, aralkyl group, aryl group, or heterocyclic group; an alkyl group, alkenyl group, alkynyl group, aralkyl group, or amino group bonded through a substituted or unsubstituted arylene group or divalent heterocyclic group; a substituted silyl group; an ether group; a thioether group; and a carbonyl group. Examples of the substituted or unsubstituted amino group include, but are not limited to: an amino group; an N-methylamino group; an N-ethylamino group; an N,N-dimethylamino group; an N,N-diethylamino group; an N-methyl-N-ethylamino group; an N-benzylamino group; an N-methyl-N-benzylamino group; an N,N-dibenzylamino group; an anilino group; an N,N-diphenylamino group; an N-phenyl-N-tolylamino group; an N,N-ditolylamino group; an N-methyl-N-phenylamino group; an N,N-dianisolylamino group; an N-mesityl-N-phenylamino group; an N,N-dimesitylamino group; an N-phenyl-N-(4-tert-butylphenyl)amino group; and an N-phenyl-N-(4-trifluoromethylphenyl)amino group.

Examples of a substituted or unsubstituted alkoxy group include: an alkyloxy group or aralkyloxy group having the above-mentioned substituted or unsubstituted alkyl group or aralkyl group; and an aryloxy group having the above-mentioned substituted or unsubstituted aryl group or heterocyclic group. Specific examples thereof include, but are not limited to: a methoxy group; an ethoxy group; a propoxy group; a 2-ethyl-octyloxy group; a phenoxy group; a 4-tert-butylphenoxy group; a benzyloxy group; and a thienyloxy group.

Examples of a substituted or unsubstituted sulfide group include: an alkylsulfide group or aralkylsulfide group having the above-mentioned substituted or unsubstituted alkyl group or aralkyl group; and an arylsulfide group having the above-mentioned substituted or unsubstituted aryl group or heterocyclic group. Specific examples thereof include, but are not limited to: a methylsulfide group; an ethylsulfide group; a phenylsulfide group; and a 4-methylphenylsulfide group.

The term "a group bonded through a linking group" herein employed refers to, for example, the "-Ph-O-Ph-" portion of Exemplified Compound No. 17 of the representative examples of the first compound as shown below, in which the ether group "—O—" is a linking group.

Examples of a linking group bonding the above-mentioned substituents include, but are not limited to: the above-mentioned substituted or unsubstituted arylene group, divalent heterocyclic group, alkylene group, alkenylene group, alkynylene group, or aralkylene group; a substituted silyl group; an ether group; a thioether group; and a carbonyl group.

Examples of a substituent which may be included in the above-mentioned substituents and linking group include, but are not limited to: a deuterium atom; an alkyl group or aralkyl group such as a methyl group, an ethyl group, an n-propyl group, an n-butyl group, an n-pentyl group, an n-hexyl group, an n-heptyl group, an n-octyl group, an n-decyl group, an iso-propyl group, an iso-butyl group, a sec-butyl group, a tert-butyl group, an iso-pentyl group, a neopentyl group, a tert-octyl group, a benzyl group, or a 2-phenylethyl group; an alkoxy group such as a methoxy group, an ethoxy group, a propoxy group, a 2-ethyl-octyloxy group, a phenoxy group, a 4-tert-butylphenoxy group, or a benzyloxy group; an aryl group such as a phenyl group, a 4-methylphenyl group, a 4-ethylphenyl group, a 3-chlorophenyl group, a 3,5-dimethylphenyl group, a triphenylamino group, a biphenyl group, a terphenyl group, a naphthyl group, an anthryl group, a phenanthryl group, or a pyrenyl group; a heterocyclic group such as a pyridyl group, a bipyridyl group, a methylpyridyl group, a thienyl group, a terthienyl group, a propylthienyl group, a furyl group, a quinolyl group, a carbazolyl group, or an N-ethylcarbazolyl group; a halogen group; a hydroxyl group; a cyano group; and a nitro group.

Preferred examples of the pyrene compound of the present invention include: a compound in which $Z_1$ represents a direct single bond and m=1, that is, a compound represented by the following general formula (2); a compound in which $X_2$ represents a direct single bond, that is, a compound represented by the following general formula (3) or (4); a compound represented by the following general formula (5) in which a substituent is introduced into at least a 7-position of the pyrene ring; and a compound having a tert-butyl group as a steric hindrance group at a 7-position of the pyrene ring, that is, a compound represented by the following general formula (6).

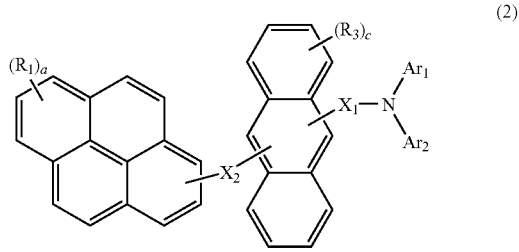

(2)

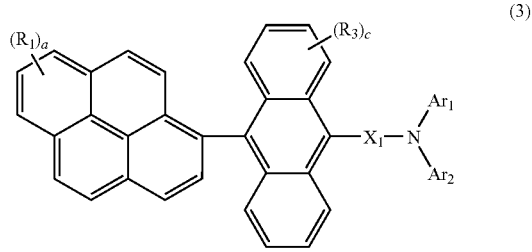

(3)

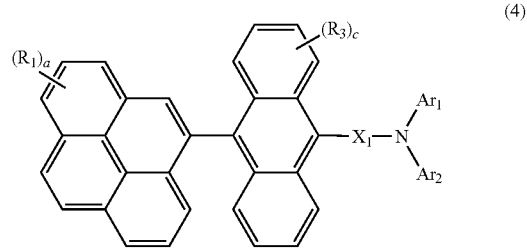

(4)

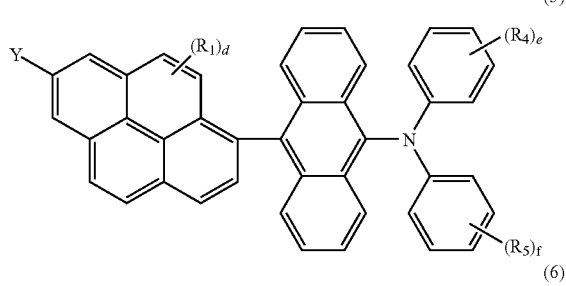

(5)

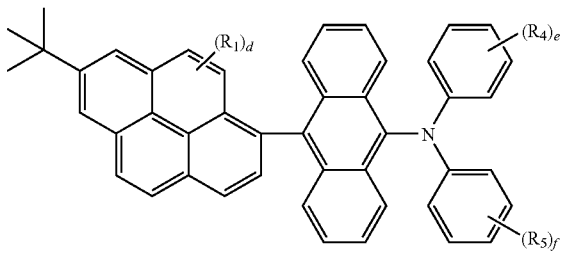

(6)

(In the general formulae: $R_4$ and $R_5$ each represent a group selected from the group consisting of a hydrogen atom, a deuterium atom, a halogen atom, a substituted or unsubstituted alkyl group, a substituted or unsubstituted aryl group, a substituted or unsubstituted alkoxy group, and a substituted or unsubstituted amino group; $R_4$ and $R_5$ may be identical to or different from each other;

d represents an integer of 1 to 8; and e and f each represent an integer of 1 to 5).

A more preferred example of the pyrene compound of the present invention is a compound in which $Z_1$ represents a phenylene group, that is, a compound represented by the following general formula (7). A particularly preferred example of the pyrene compound of the present invention is a compound in which $Z_1$ represents a metaphenylene group, b=1, and m=1, that is, a compound represented by the following general formula (8) or (9). Especially preferred examples thereof include: a compound represented by the following general formula (10) in which a substituent is introduced into at least a 7-position of the pyrene ring; and a compound having a tert-butyl group as a steric hindrance group at a 7-position of the pyrene ring, that is, a compound represented by the following general formula (11).

(7)

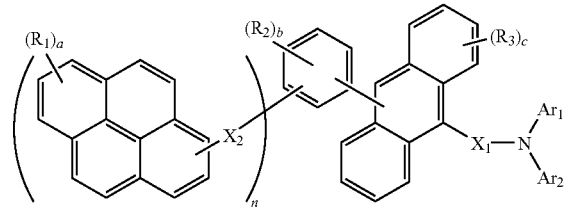

(8)

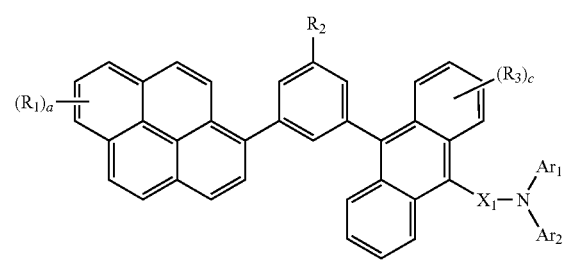

(9)

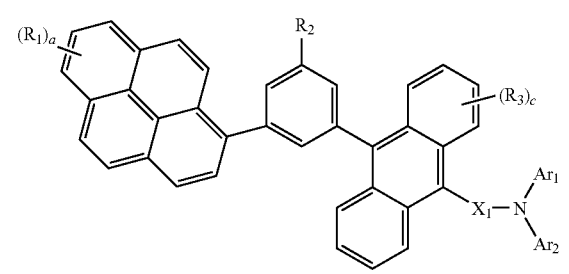

-continued (10)

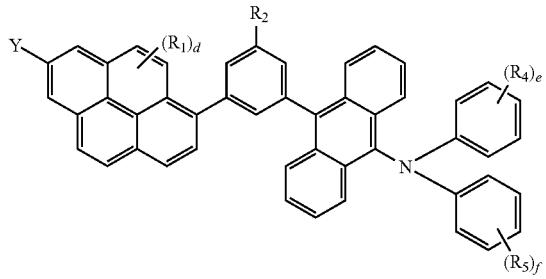

(11)

(In the general formulae: $R_4$ and $R_5$ each represent a group selected from the group consisting of a hydrogen atom, a deuterium atom, a halogen atom, a substituted or unsubstituted alkyl group, a substituted or unsubstituted aryl group, a substituted or unsubstituted alkoxy group, and a substituted or unsubstituted amino group; $R_4$ and $R_5$ may be identical to or different from each other;

d represents an integer of 1 to 8; and e and f each represent an integer of 1 to 5).

Specific examples of the substituted or unsubstituted alkyl group, aryl group, alkoxy group, or amino group in the general formulae (5), (6), (10), and (11) include those described for the general formula (1).

Next, typical examples of the pyrene compound of the present invention will be described. However, the pyrene compound of the present invention is not limited to those compounds.

1

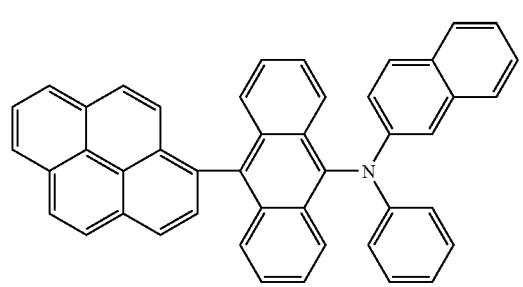

2

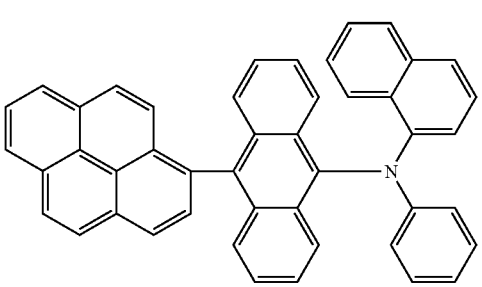

-continued
3
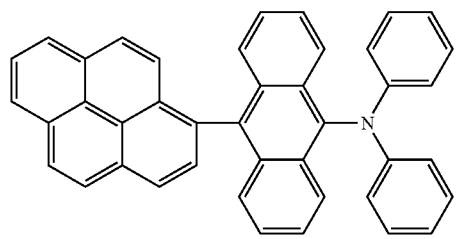
4
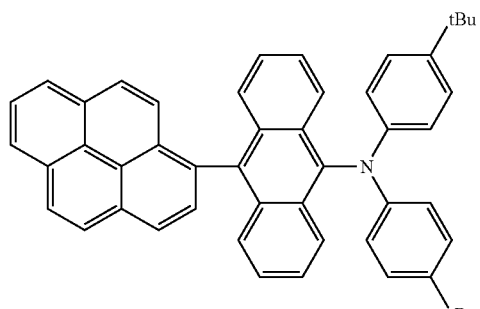
5
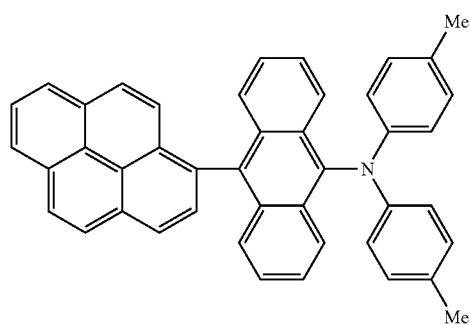
6
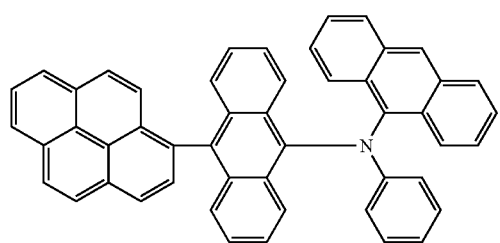
7
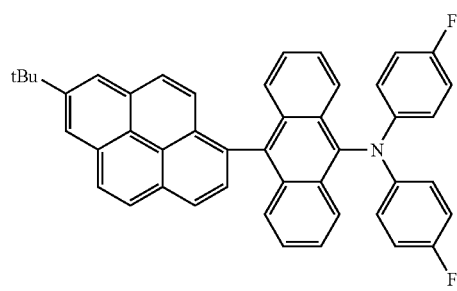
8
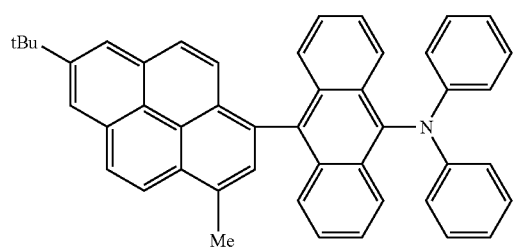
9
10
11
12
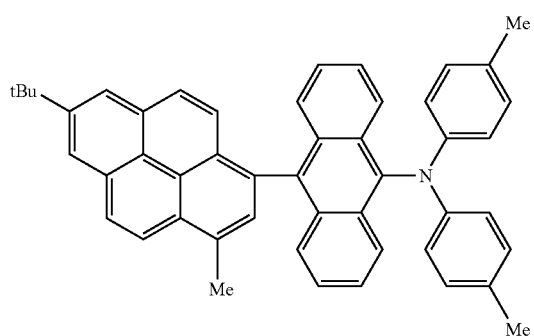

-continued
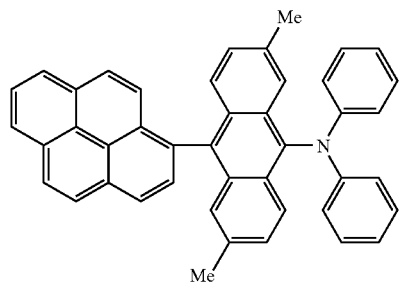
13
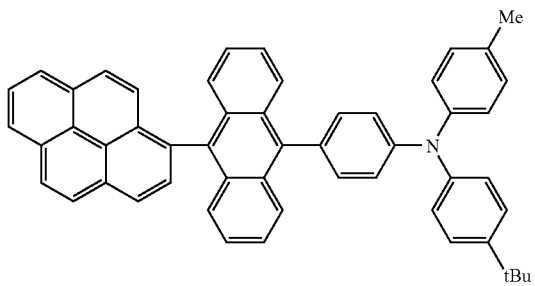
14
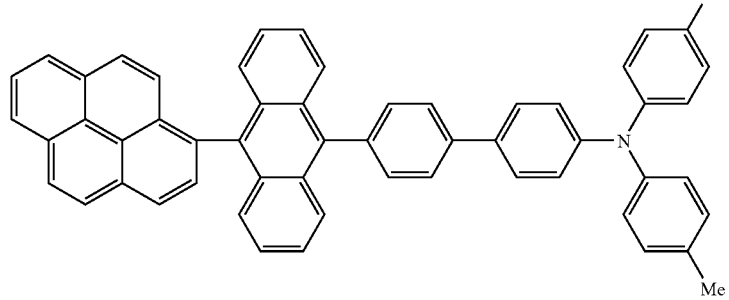
15
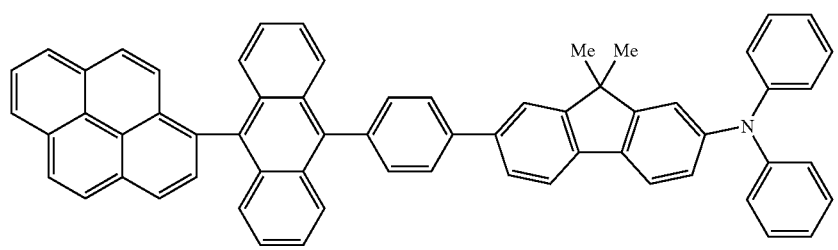
16
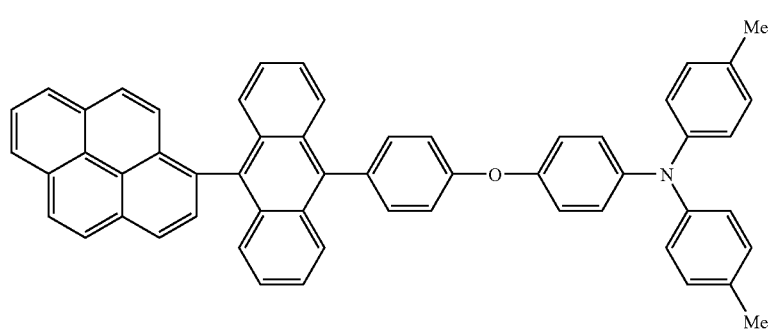
17
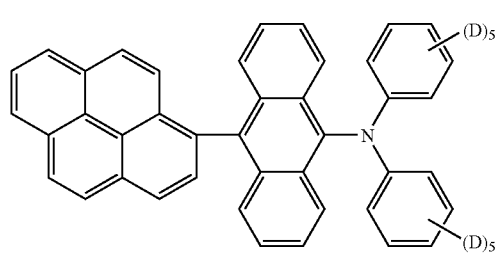
18
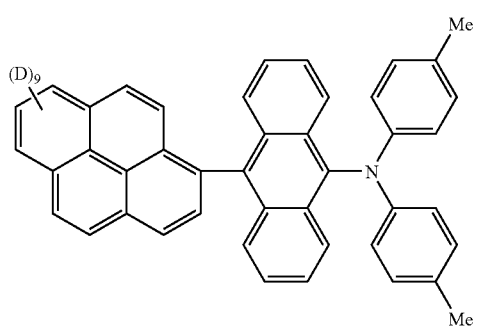
19

-continued
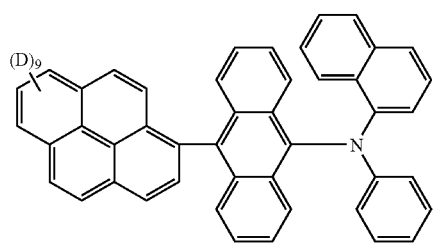
20
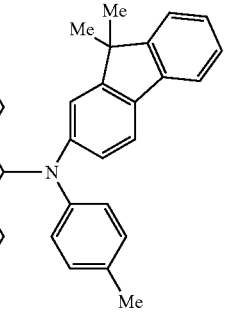
21
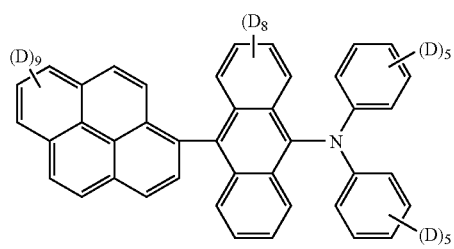
22
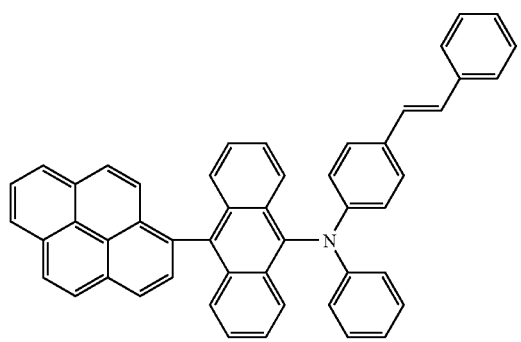
23
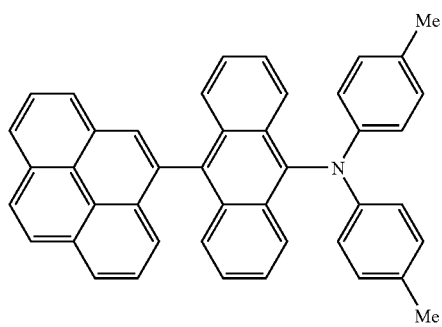
24
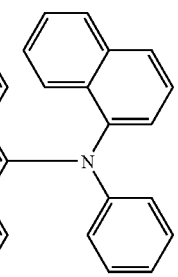
25
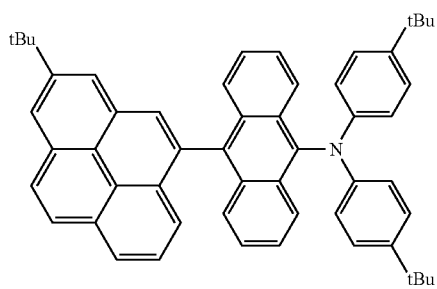
26
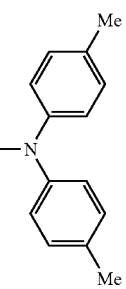
27
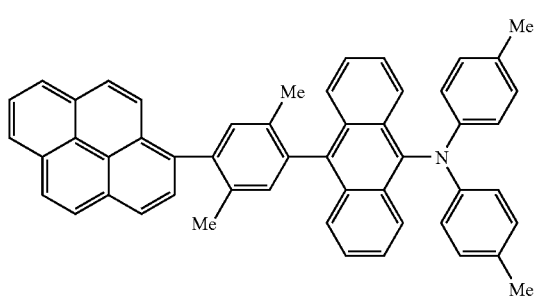
28
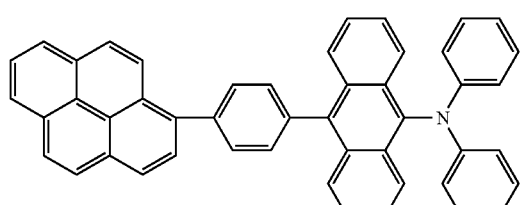
29

-continued
30
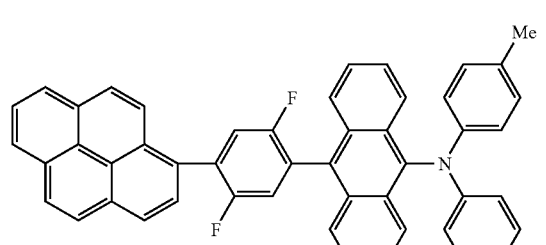
31
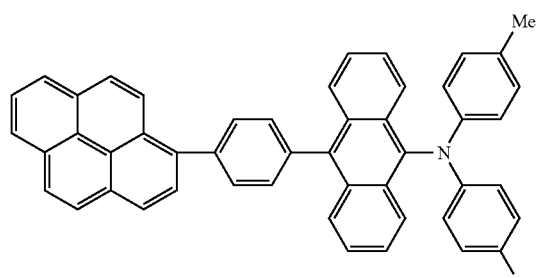
32
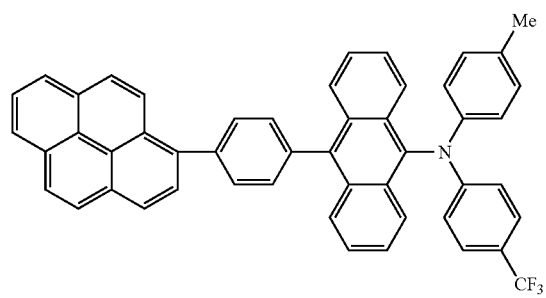
33
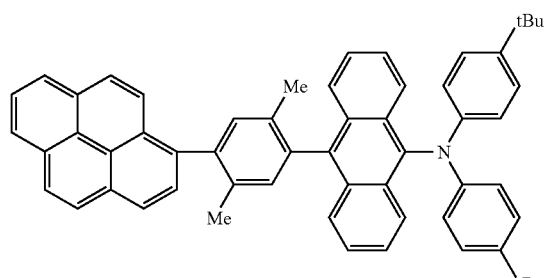
34
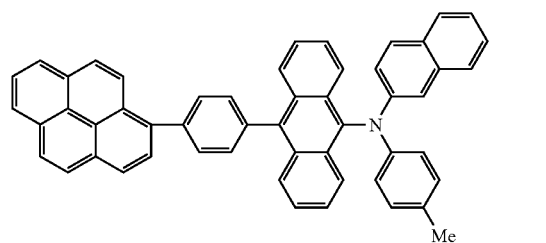
35
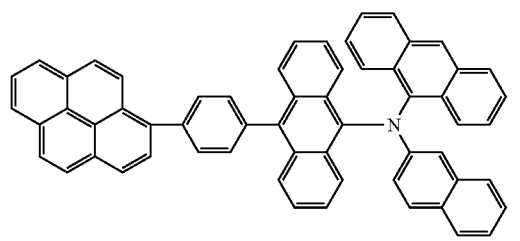
36
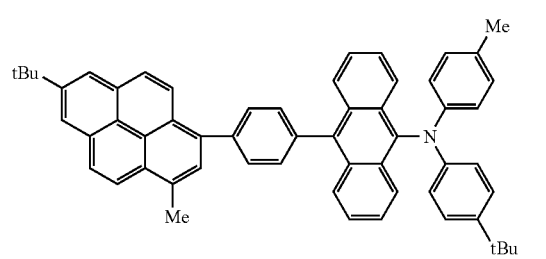
37
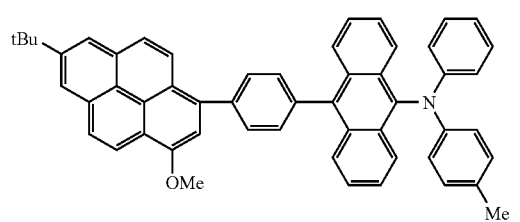
38
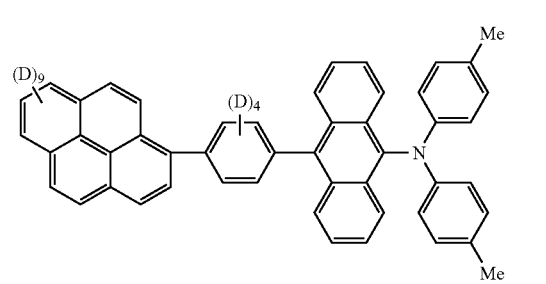
39
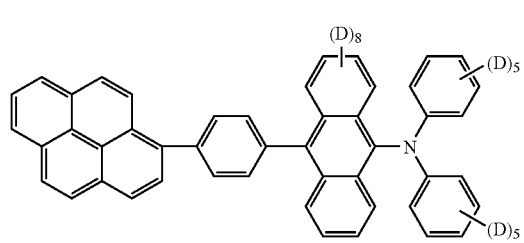
40
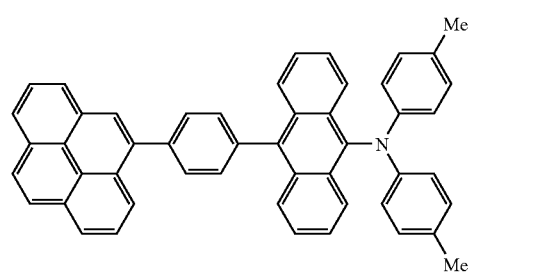
41
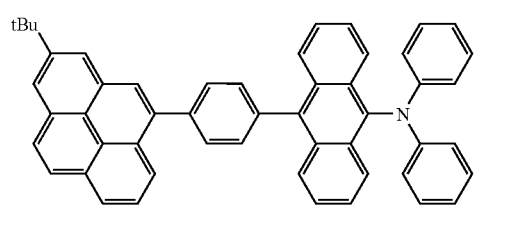

-continued
42
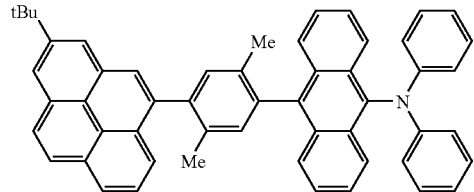
43
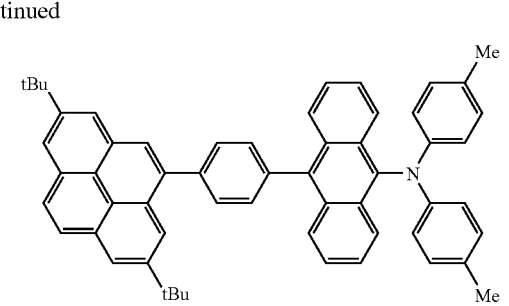
44
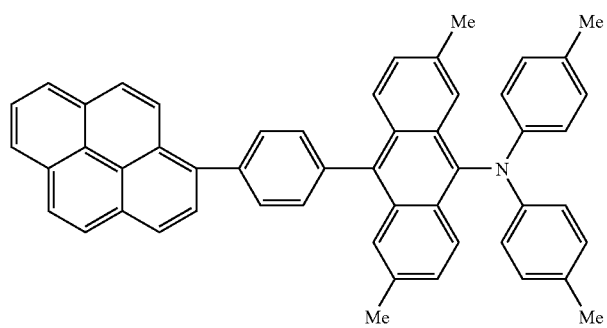
45
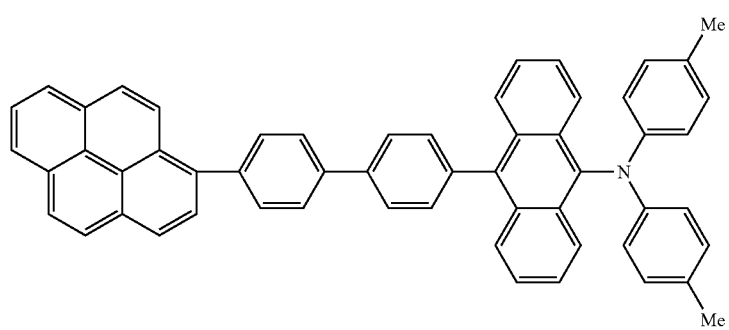
46
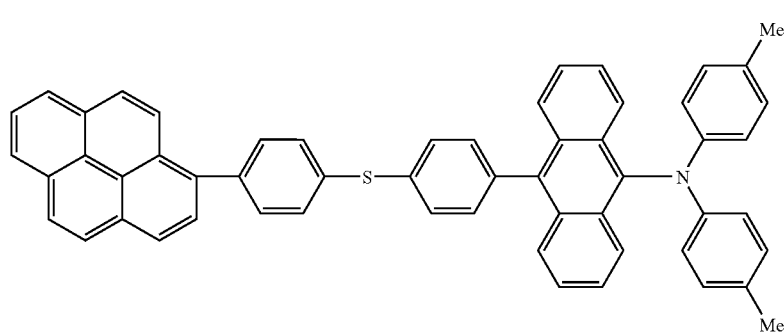
47
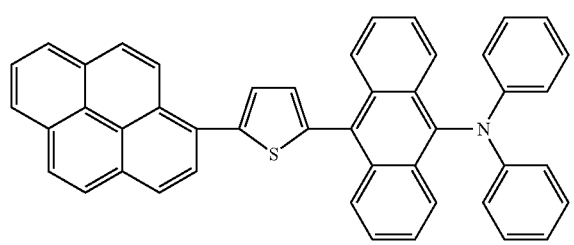
48
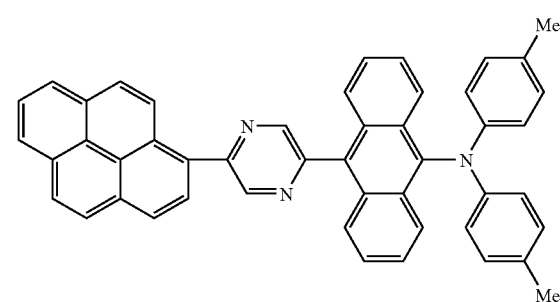

-continued
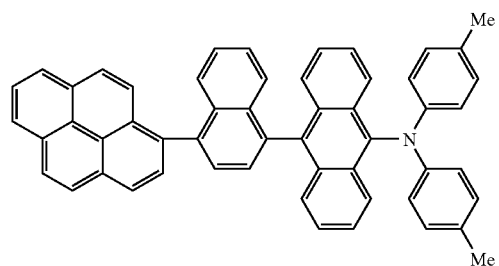
49
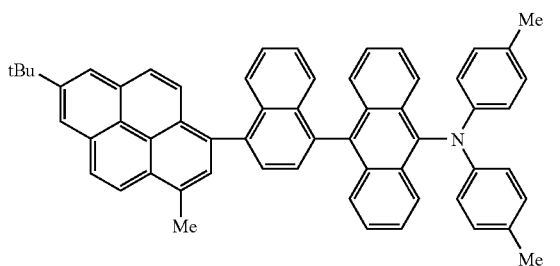
50
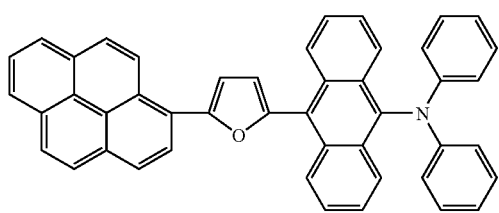
51
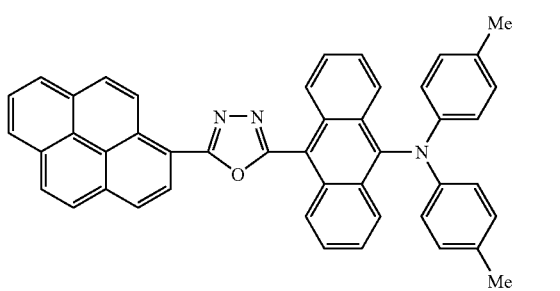
52
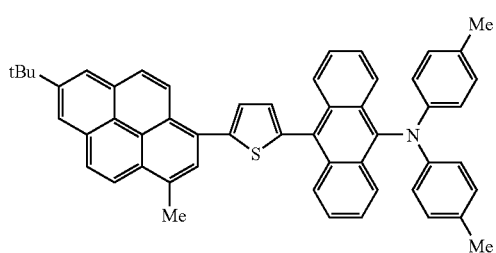
53
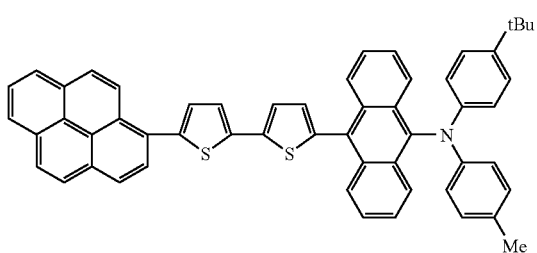
54
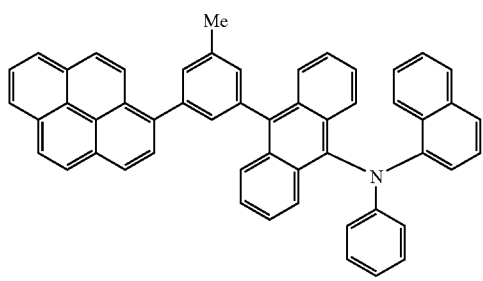
55
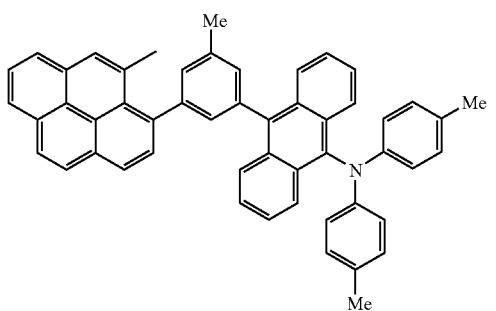
56
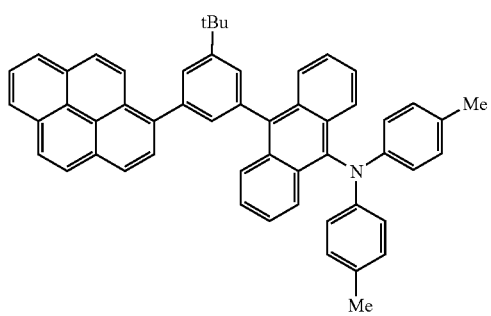
57
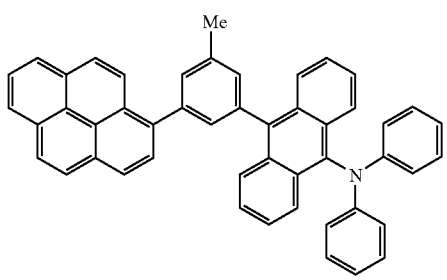
58

-continued
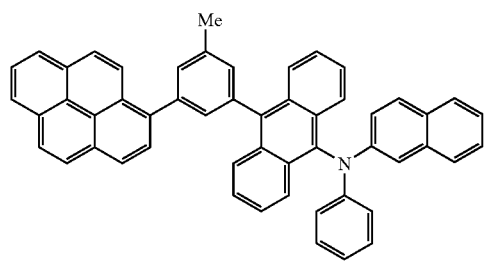
59
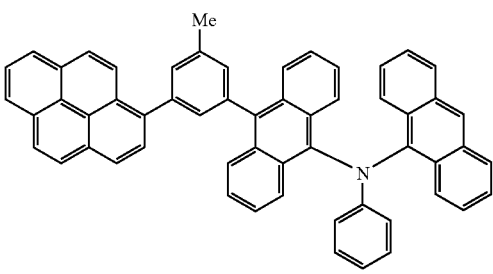
60
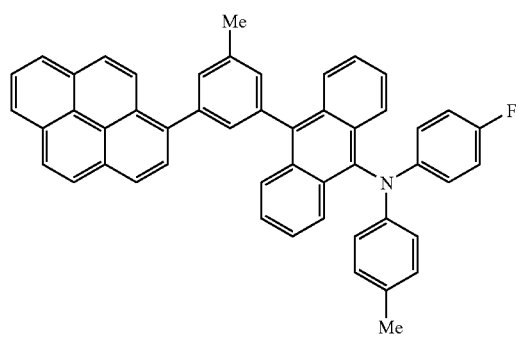
61
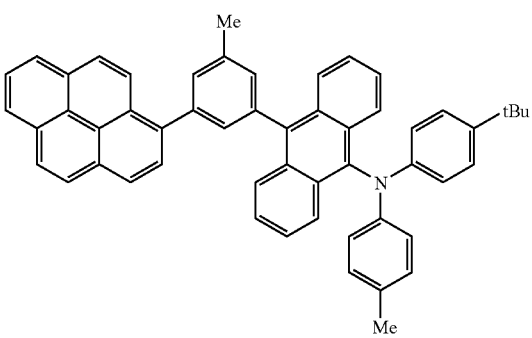
62
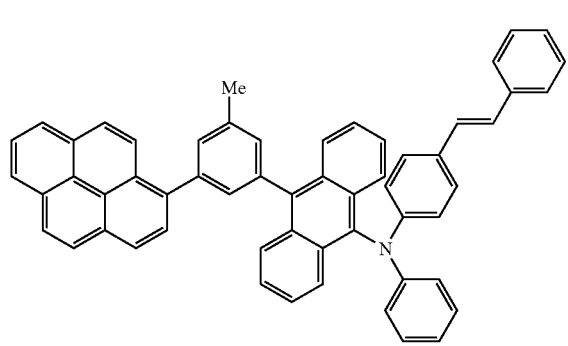
63
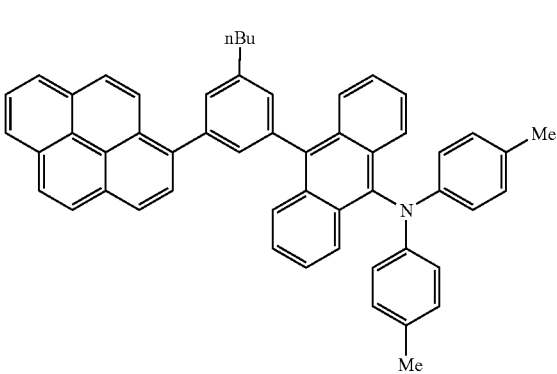
64
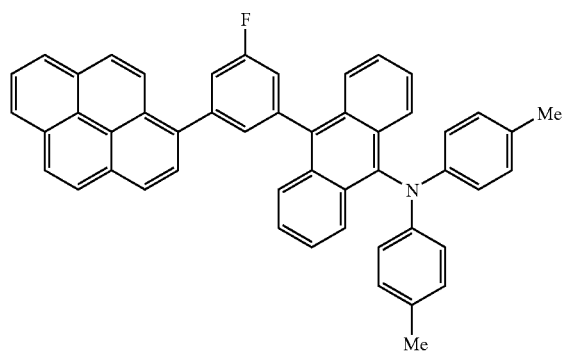
65
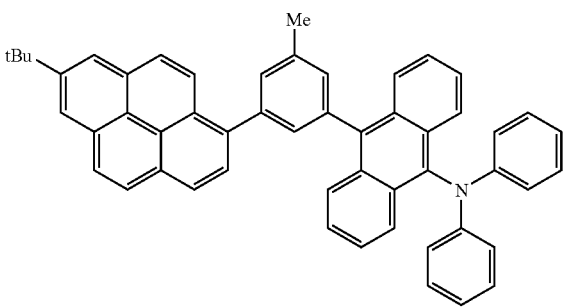
66

-continued
67
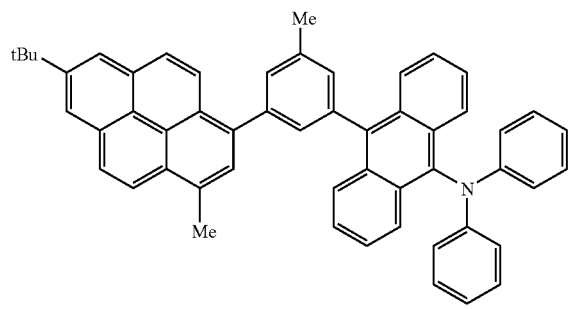
68
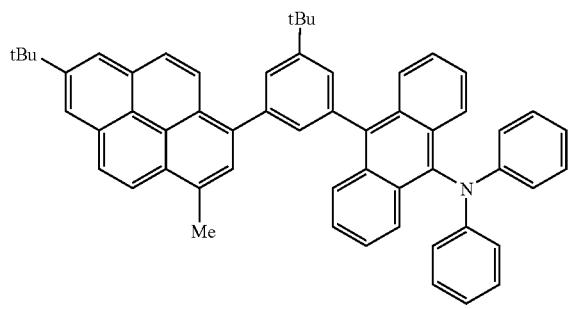
69
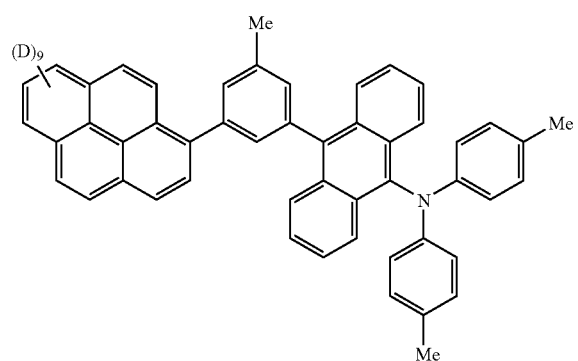
70
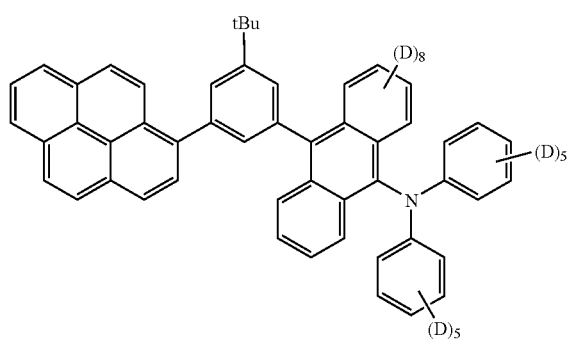
71
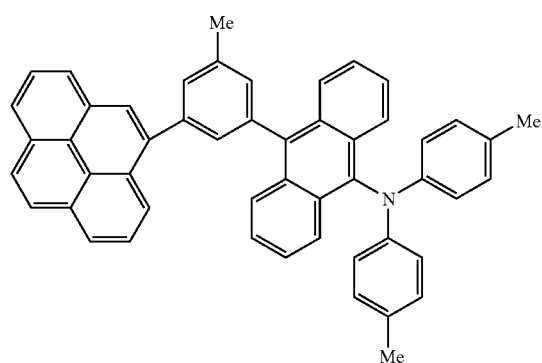
72
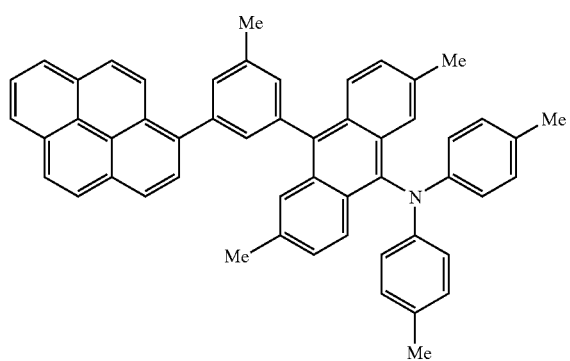
73
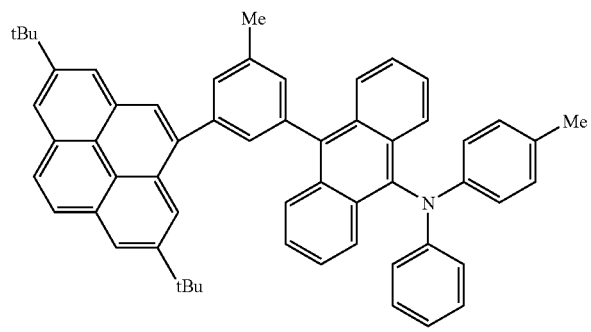
74
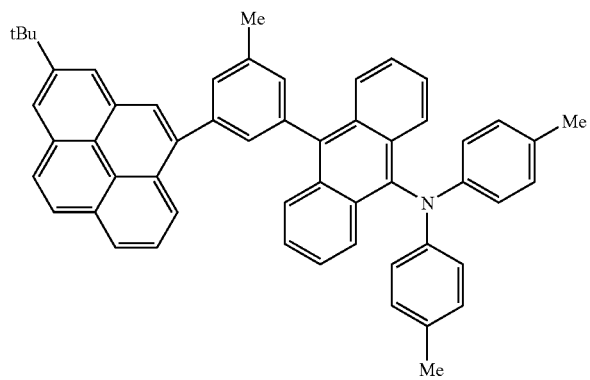

-continued
75 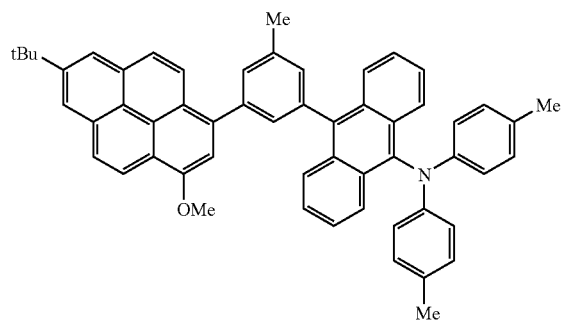
76 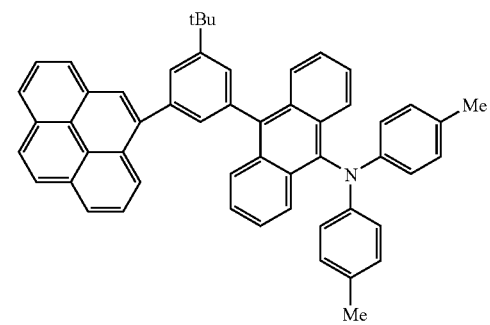
77 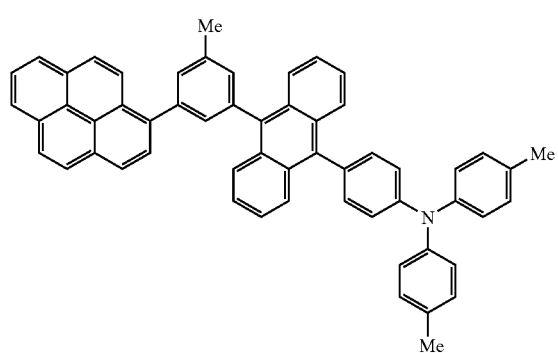
78 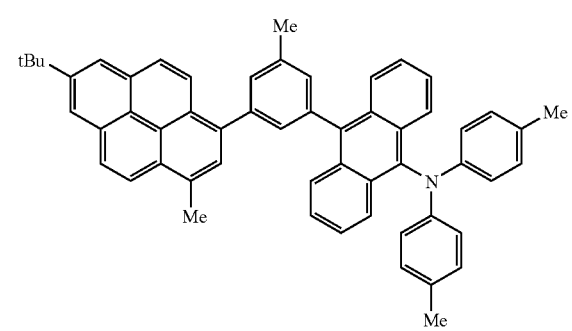
79 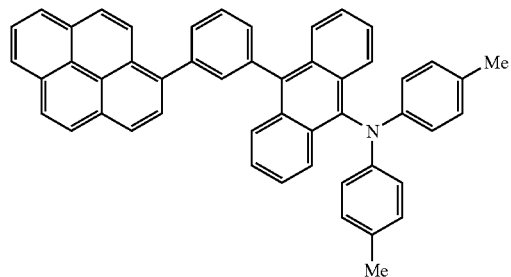
80
81 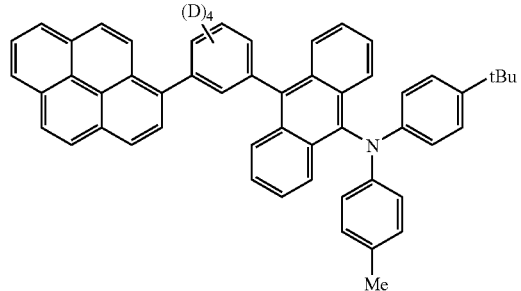
82
83 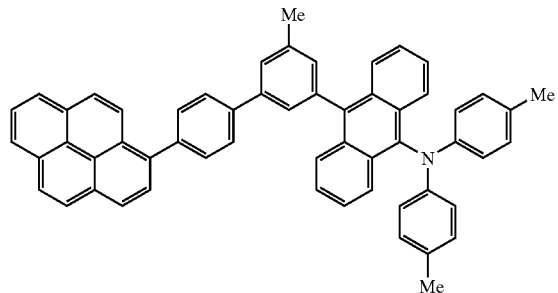
84 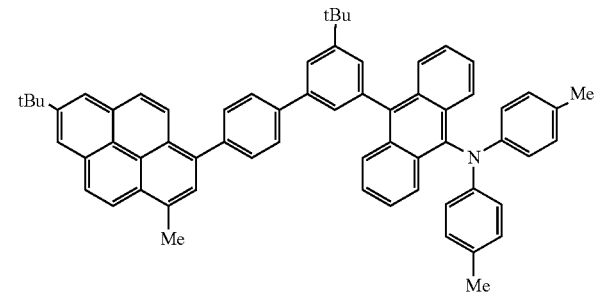

-continued
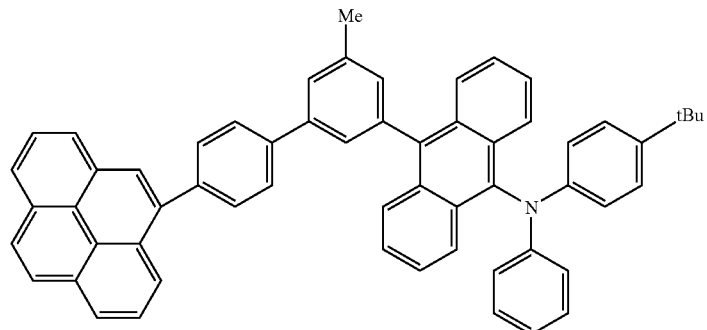
85
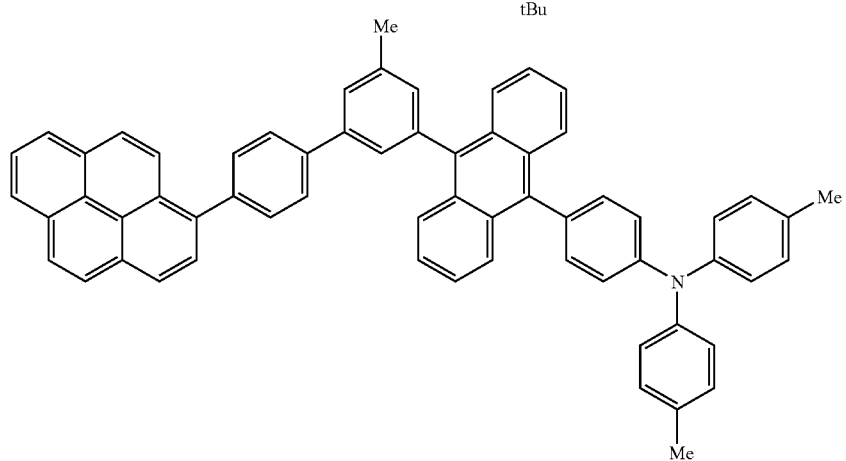
86
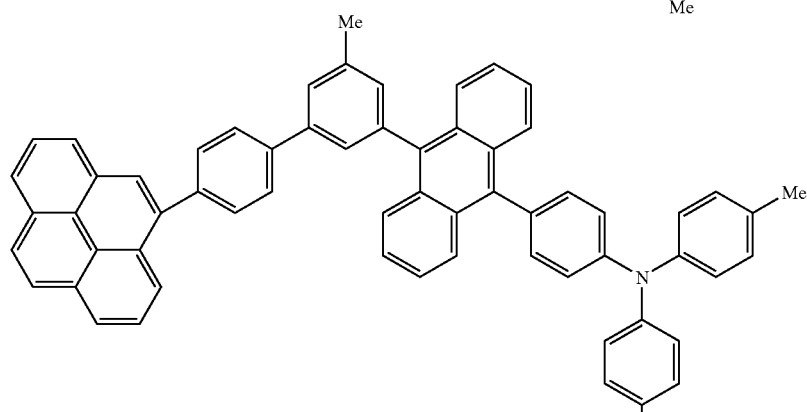
87
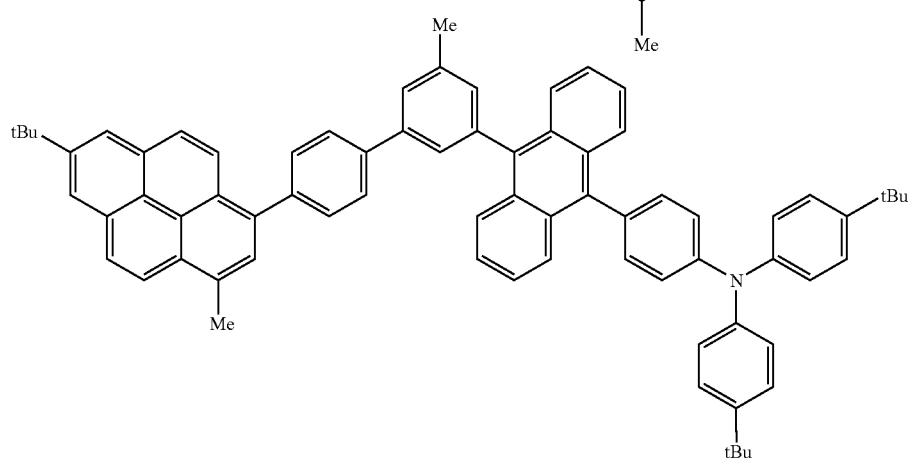
88

-continued
89
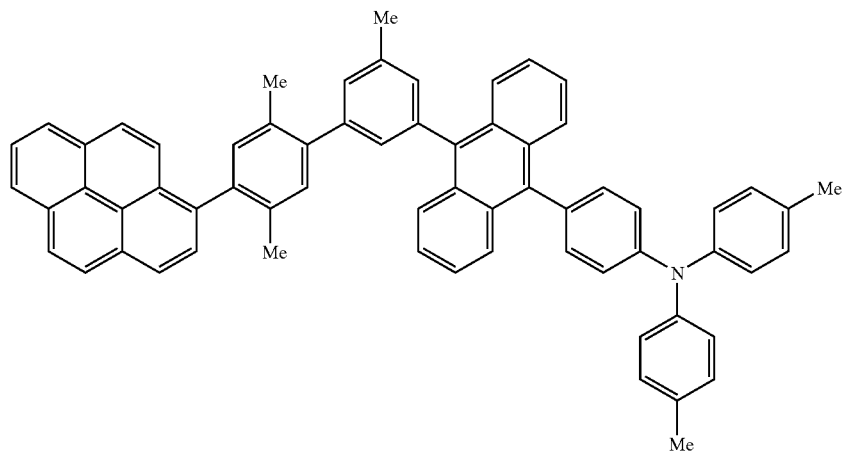
90
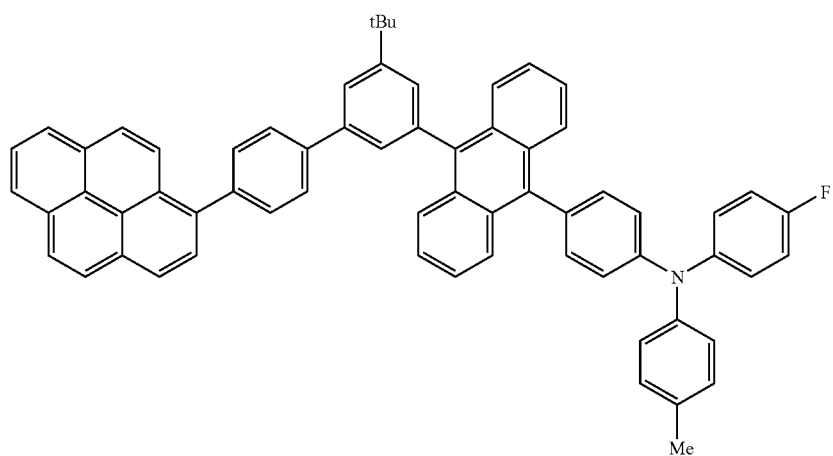
91
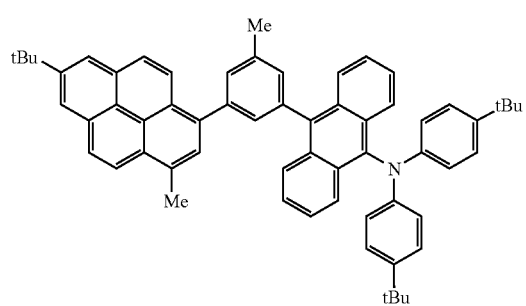
92
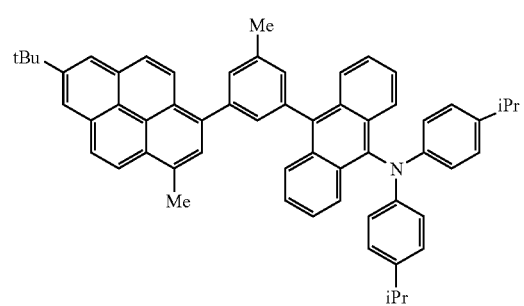
93
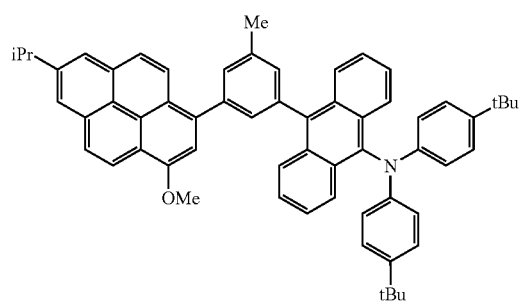
94
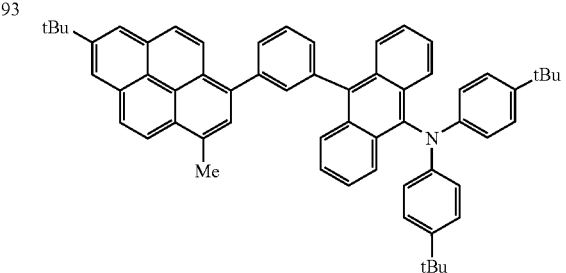

-continued
95
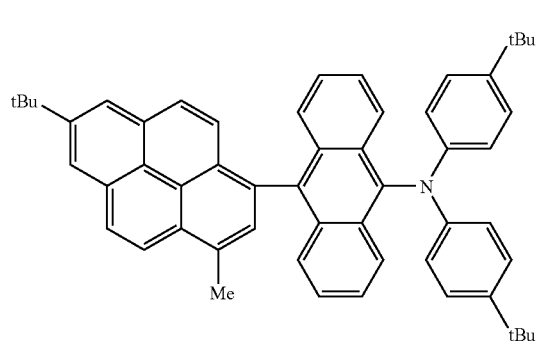
96
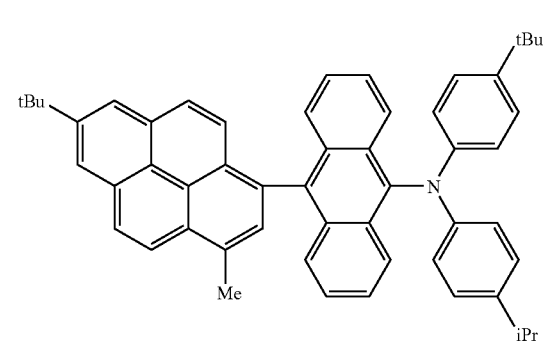
97
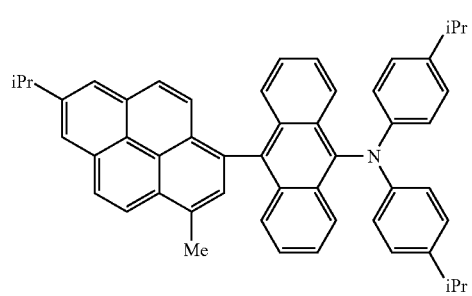
98
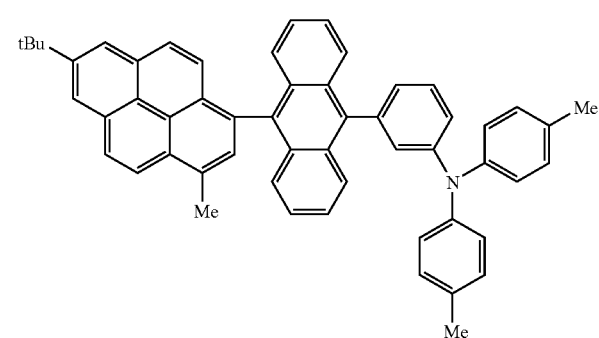
99
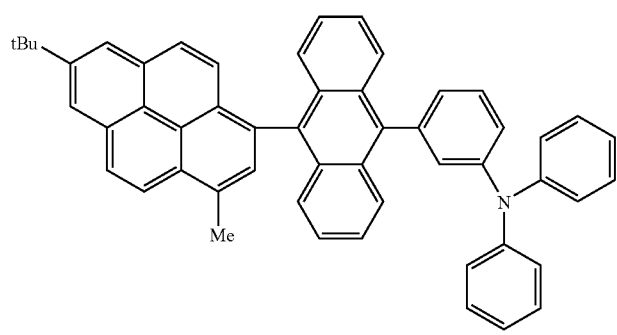
100
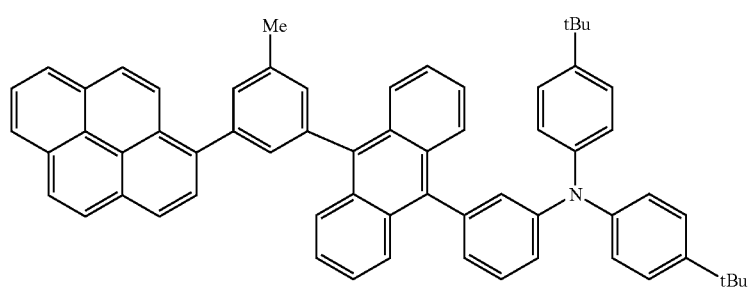
101
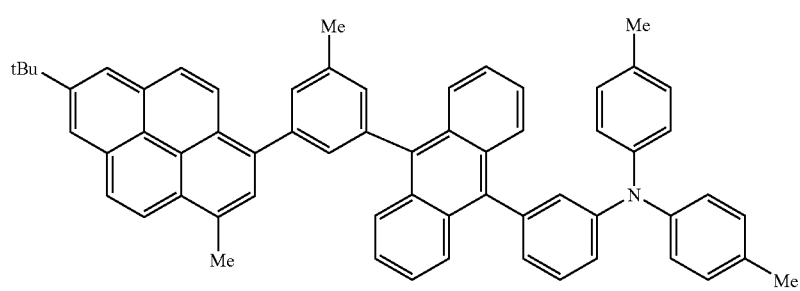

-continued
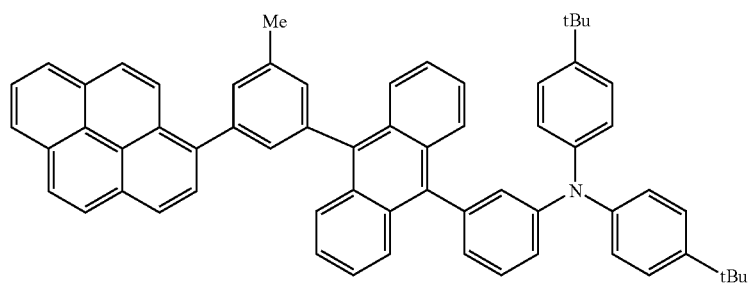
100
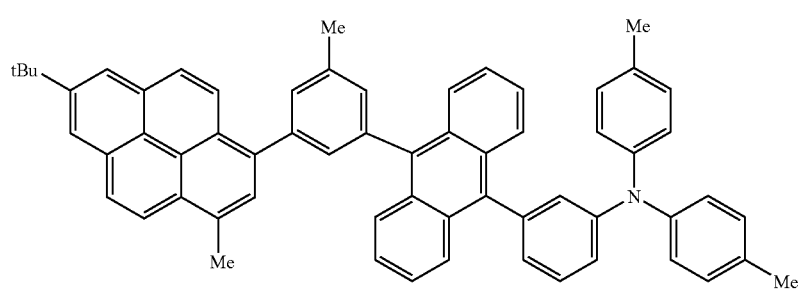
101
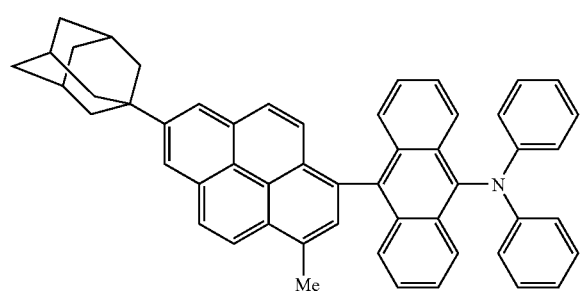
102
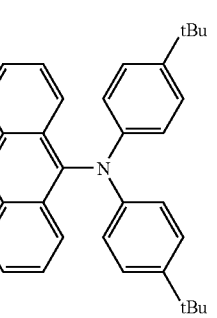
103
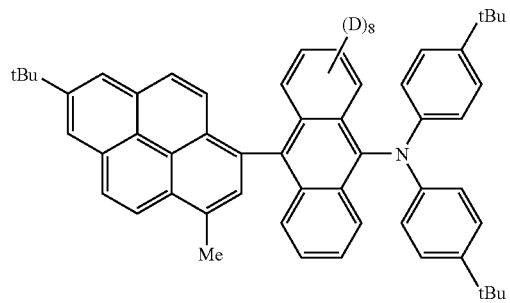
104
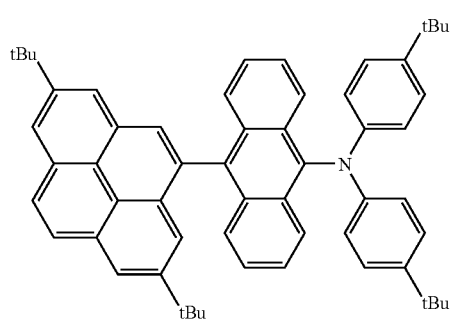
105
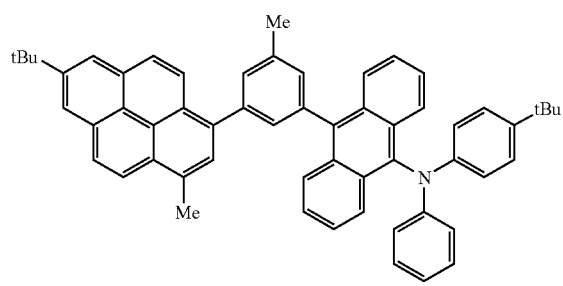
106
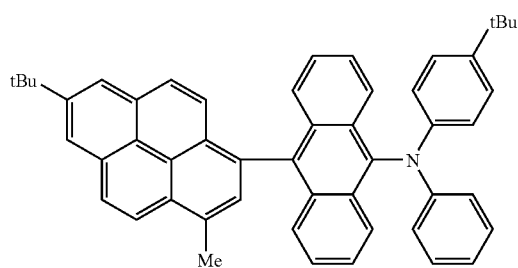
107

Next, an organic light-emitting device of the present invention will be described in more detail.

The organic light-emitting device of the present invention includes: a pair of electrodes consisting of an anode and a cathode; and a layer or a plurality of layers each containing an organic compound and held between the pair of electrodes. In the organic light-emitting device, at least one of the layers each containing an organic compound, preferably a light emission layer, contains at least one pyrene compound of the present invention.

FIGS. 1 to 5 show preferred examples of the organic light-emitting device of the present invention.

FIG. 1 is a sectional view showing an example of an organic light-emitting device according to the present invention. As shown in FIG. 1, the organic light-emitting device has a structure in which an anode 2, a light emission layer 3, and a cathode 4 are provided on a substrate 1 in the order given. The light-emitting device used herein is useful in the case where the device itself has hole transport property, electron transport property, and light emission property or where compounds having the respective properties are used in combination.

Figure 2:
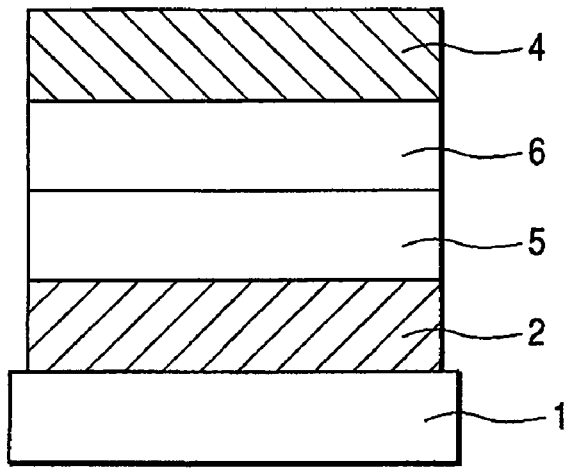
FIG. 2 is a sectional view showing another example of the organic light-emitting device according to the present invention.

FIG. 2 is a sectional view showing another example of the organic light-emitting device according to the present invention. As shown in FIG. 2, the organic light-emitting device has a structure in which the anode 2, a hole transport layer 5, an electron transport layer 6, and the cathode 4 are provided on the substrate 1 in the order given. A light-emitting substance is useful in the case where a material having one or both of hole transport property and electron transport property is used for each layer, and the light-emitting substance is used in combination with a non-illuminant hole transport substance or electron transport substance. In this case, the light emission layer is formed of the hole transport layer 5 or the electron transport layer 6.

Figure 3:
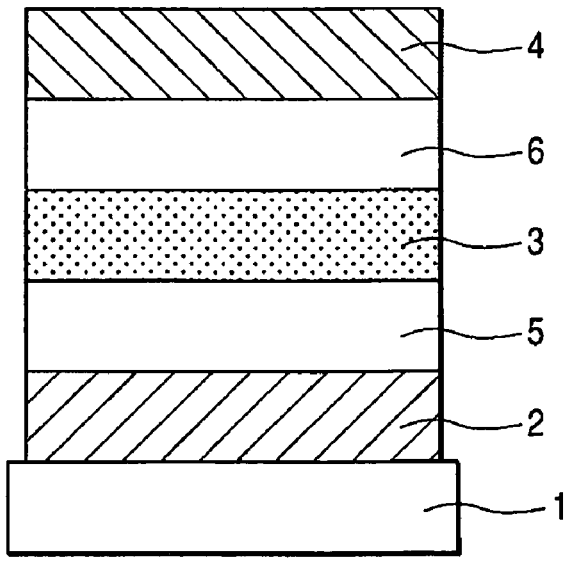
FIG. 3 is a sectional view showing still another example of the organic light-emitting device according to the present invention.

FIG. 3 is a sectional view showing still another example of the organic light-emitting device according to the present invention. As shown in FIG. 3, the organic light-emitting device has a structure in which the anode 2, the hole transport layer 5, the light emission layer 3, the electron transport layer 6, and the cathode 4 are provided on the substrate 1 in the order given. This organic light-emitting device has separate carrier transport function and light-emitting function. The device is used in combination with compounds each having hole transport property, electron transport property, or light emission property as appropriate, thereby allowing substantial increase in freedom of choice in material to be used. Further, various compounds having different emission wavelengths can be used, thereby allowing increase in variety of luminescent colors. Further, luminous efficiency may be improved by efficiently trapping each carrier or exciton in the light emission layer 3 provided in the middle of the device.

Figure 4:
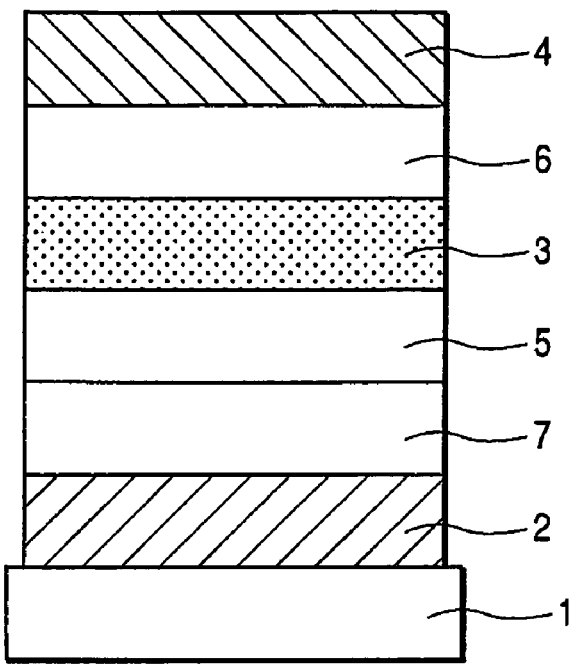
FIG. 4 is a sectional view showing yet another example of the organic light-emitting device according to of the present invention.

FIG. 4 is a sectional view showing yet another example of the organic light-emitting device according to the present invention. FIG. 4 has a structure shown in FIG. 3 except that a hole injection layer 7 is inserted into a side of the anode 2. This structure is effective for improving adhesiveness between the anode 2 and the hole transport layer 5 or for improving hole injection property, which is effective in lowering a voltage to be applied to the device. In FIG. 4, the same reference numerals as those of FIG. 3 represent the same layers.

Figure 5:
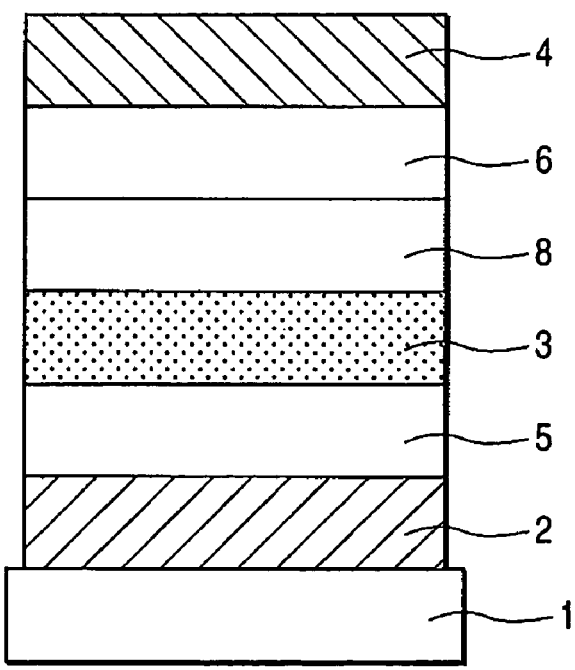
FIG. 5 is a sectional view showing still yet another example of the organic light-emitting device according to the present invention.

FIG. 5 is a sectional view showing still yet another example of the organic light-emitting device according to the present invention. FIG. 5 has a structure shown in FIG. 3 except that a layer for blocking travel of a hole or exciton to a side of the cathode 4 (a hole/exciton-blocking layer 8) is inserted between the light emission layer 3 and the electron transport layer 6. This structure uses a compound having an extremely high ionization potential for the hole/exciton-blocking layer 8 and is effective for improving luminous efficiency. In FIG. 5, the same reference numerals as those of FIG. 3 represent the same layers.

However, FIGS. 1 to 5 each show a very basic device structure, and the structure of the organic light-emitting device using the pyrene compound of the present invention is not limited to the structures shown FIGS. 1 to 5. For example, the organic light-emitting device of the present invention may have any one of various layer structures including: a structure in which an insulating layer is provided at an interface between an electrode and an organic layer; a structure in which an adhesive or interference layer is provided; and a structure in which a hole transport layer is composed of two layers with different ionization potentials.

The pyrene compound of the present invention may be used for any one of the structures shown in FIGS. 1 to 5.

In particular, an organic layer using the compound of the present invention is useful as a light emission layer, an electron transport layer, or a hole transport layer. In addition, a layer formed through a vacuum deposition method, a solution coating method, or the like is hardly crystallized and has excellent stability over time.

In the present invention, the above-mentioned pyrene compound of the present invention is particularly used as a component of the light emission layer. The compound may be used in combination with a known low molecular weight or polymer hole transport compound, light emission compound, electron transport compound, or the like as required.

Examples of the compounds will be shown below.

A preferred hole-injection transporting material has excellent mobility for facilitating injection of a hole from an anode and for transporting the injected hole to a light emission layer. Examples of a low molecular weight or polymer material having hole-injection transporting property include, but are not limited to: a triarylamine derivative; a phenylenediamine derivative; a triazole derivative; an oxadiazole derivative; an imidazole derivative; a pyrazoline derivative; a pyrazolone derivative; an oxazole derivative; a fluorenone derivative; a hydrazone derivative; a stilbene derivative; a phthalocyanine derivative; a porphyrin derivative; poly(vinylcarbazole); poly(silylene); poly(thiophene); and other conductive polymers. Specific examples thereof will be partly shown below.

Low Molecular Weight Hole-Injection Transporting Materials
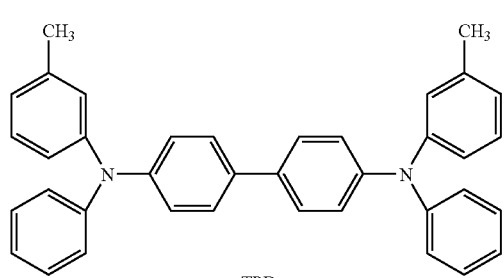
TPD
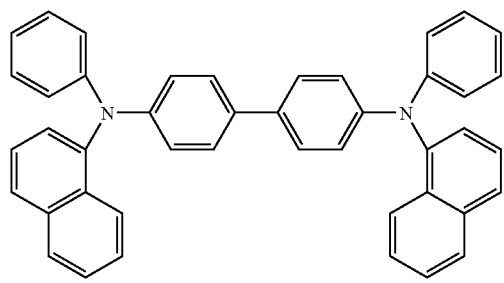
α-NPD
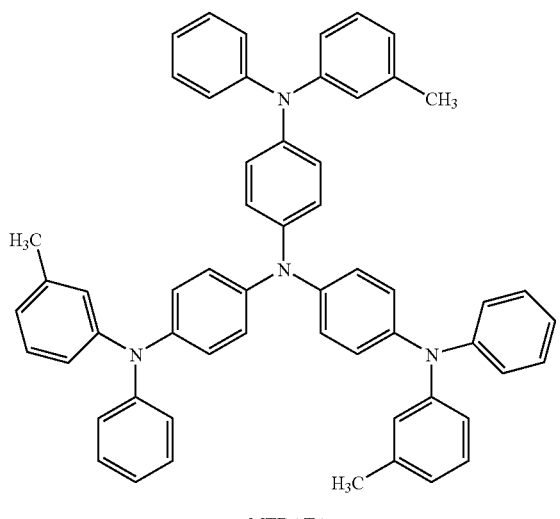
m-MTDATA
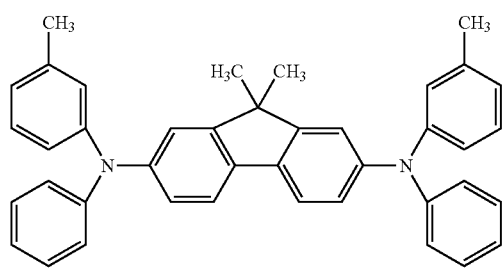
DTDPFL
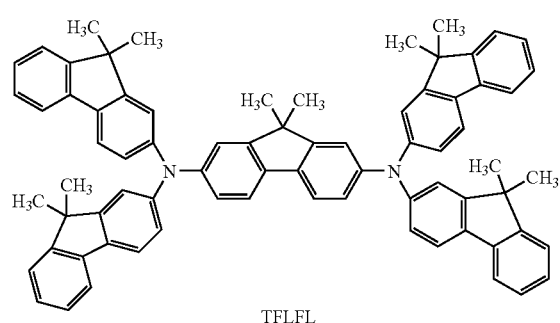
TFLFL
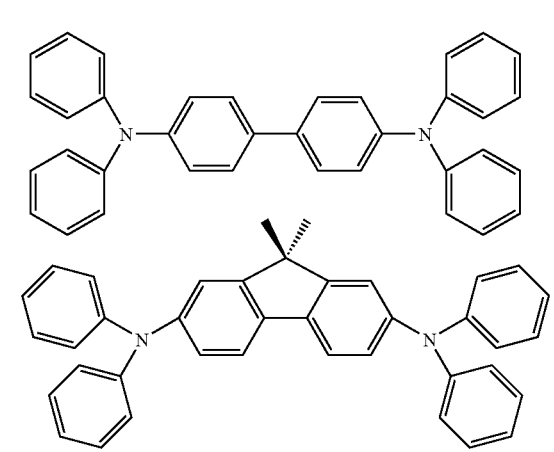
spiro-TPD
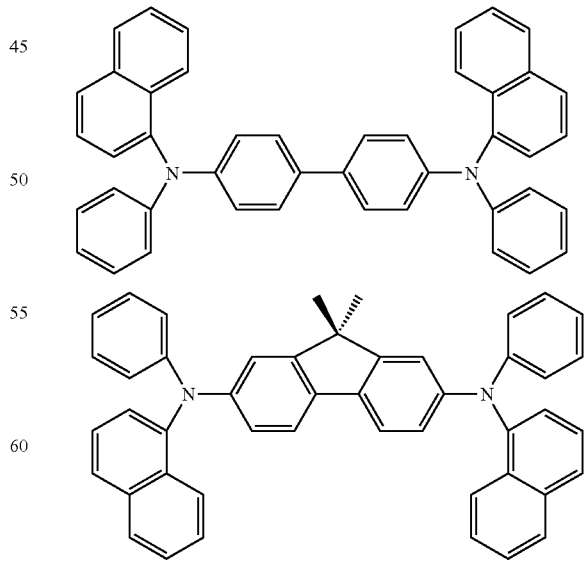
spiro-NPD -continued
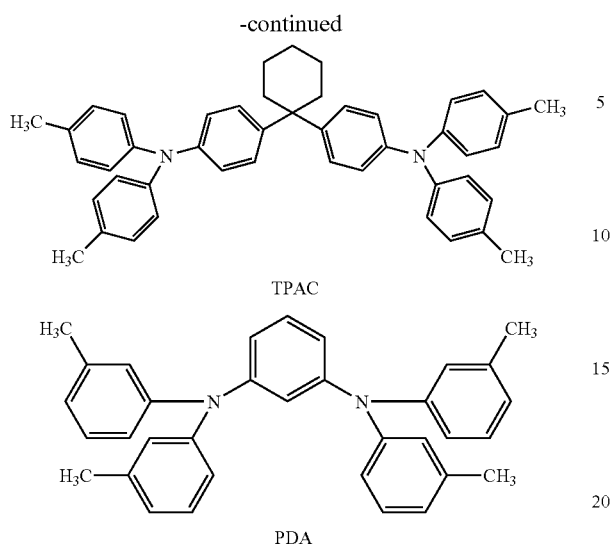
TPAC
PDA
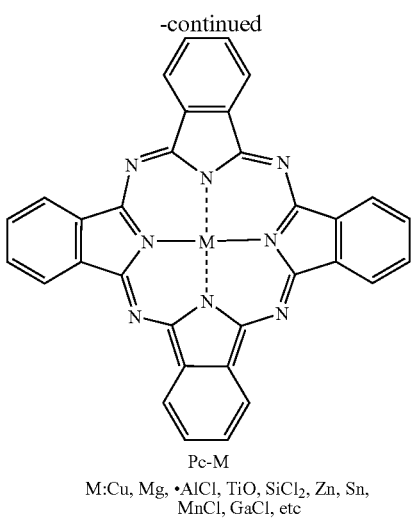
Pc-M
M:Cu, Mg, •AlCl, TiO, $SiCl_2$, Zn, Sn, MnCl, GaCl, etc
Polymer Hole Transport Materials
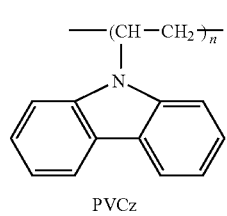
PVCz
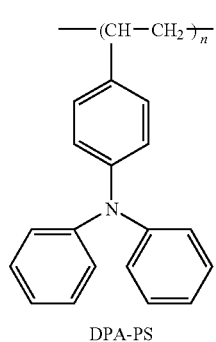
DPA-PS
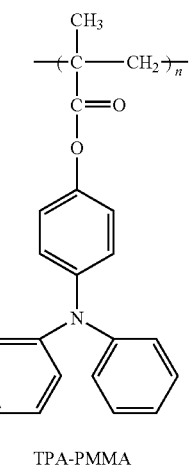
TPA-PMMA
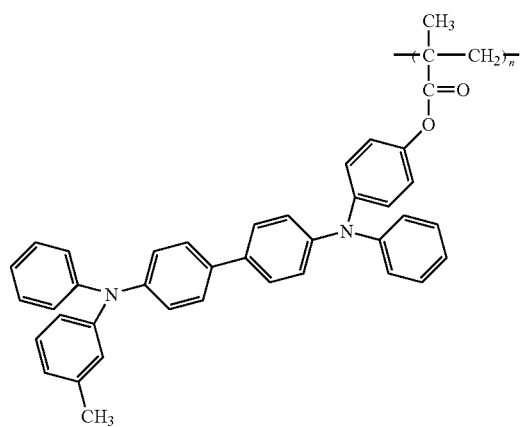
TPD-PMMA
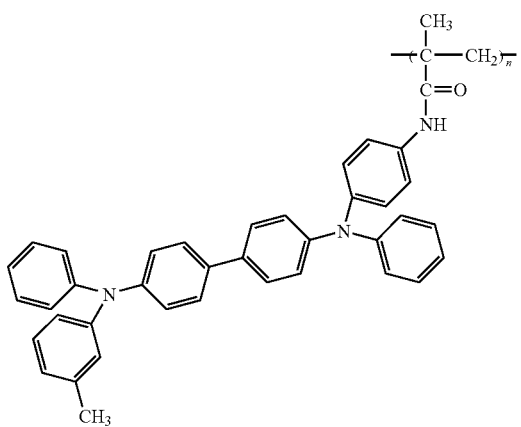
TPD-PMAA -continued

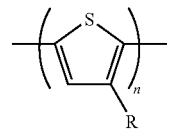

R:C$_6$H$_{13}$, C$_8$H$_{17}$, C$_{12}$H$_{25}$
Poly thiophene

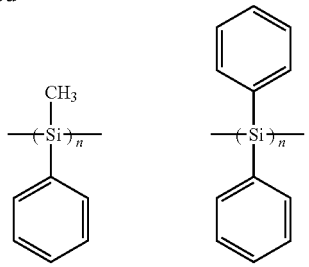

Polysilane

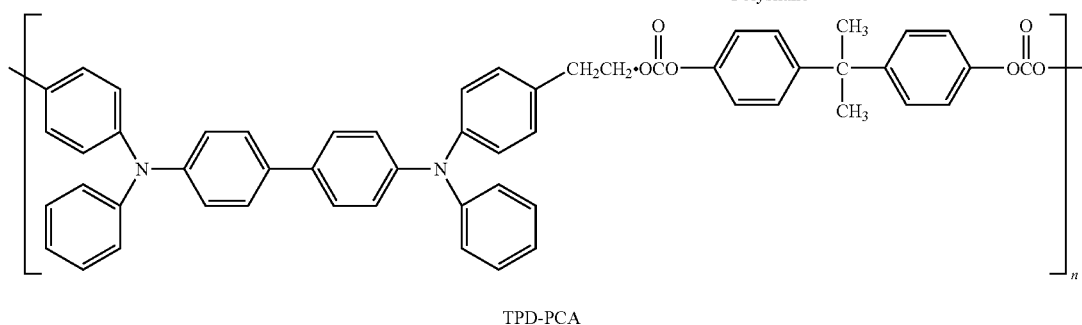

TPD-PCA

Examples of a material which is mainly involved in a light-emitting function except the pyrene compound of the present invention include, but are not limited to: a polycyclic condensed aromatic compound (including a naphthalene derivative, a phenanthrene derivative, a fluorene derivative, a pyrene derivative, a tetracene derivative, a coronene derivative, a chrysene derivative, a perylene derivative, a 9,10-diphenylanthracene derivative, or rubrene); a quinacridone derivative; an acridone derivative; a coumarin derivative; a pyran derivative; Nile red; a pyrazine derivative; a benzoimidazole derivative; a benzothiazole derivative; a benzoxazole derivative; a stilbene derivative; an organometallic complex (including: an organic aluminum complex such as tris(8-quinolinolato)aluminum; or an organic beryllium complex); and a polymer derivative (including a poly(phenylene vinylene) derivative, a poly(fluorene) derivative, a poly(phenylene) derivative, a poly(thienylene vinylene) derivative, or a poly(acetylene) derivative). Specific examples thereof will be partly shown below.

Low Molecular Weight Light-Emitting Materials

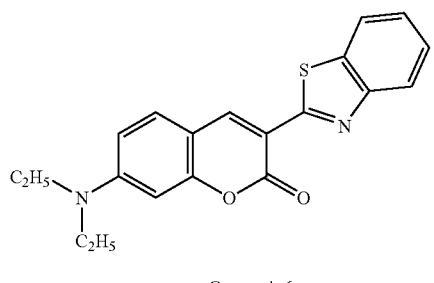

Coumarin6

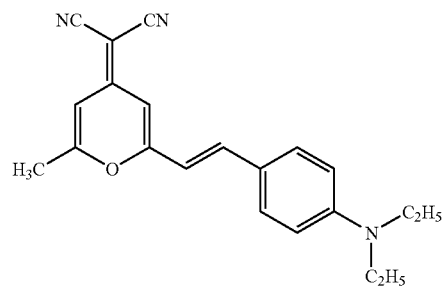

DCM-1

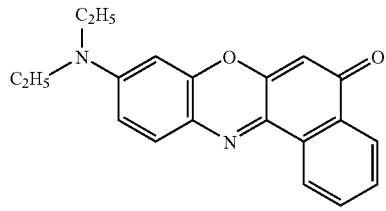

Nile red

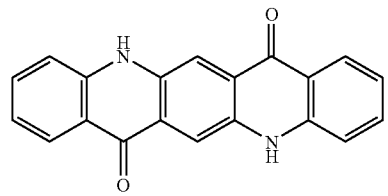

Quinacridone

-continued
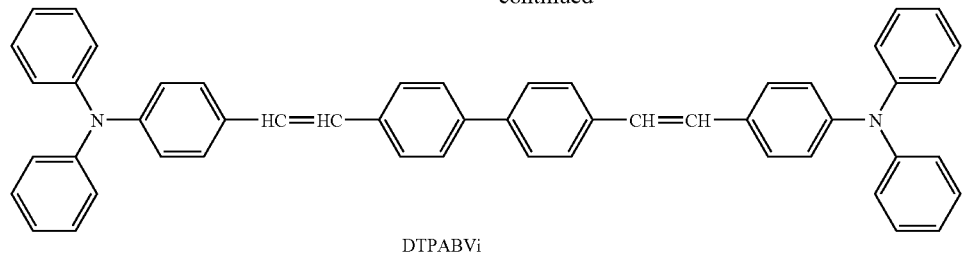
DTPABVi
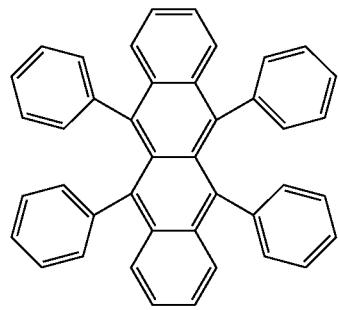
Rubrene
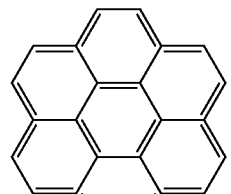
Coronene
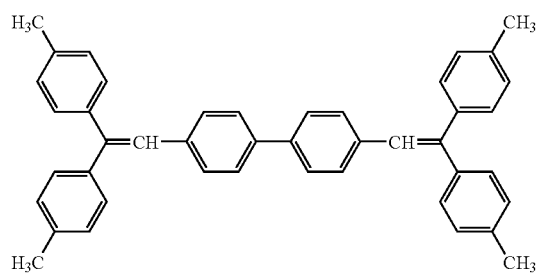
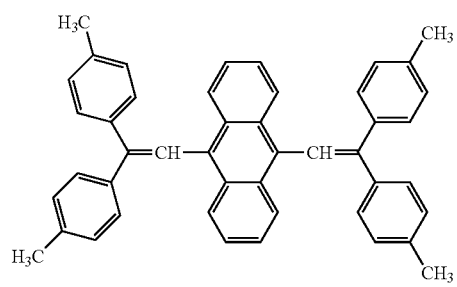
Polymer Light-Emitting Materials
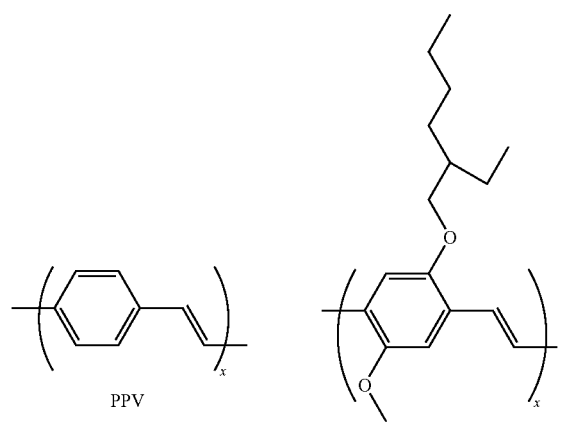
PPV
-continued
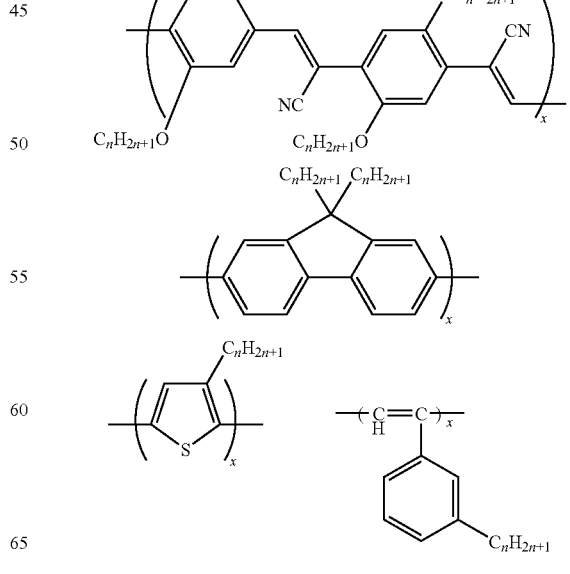

Metal Complex Light-Emitting Materials

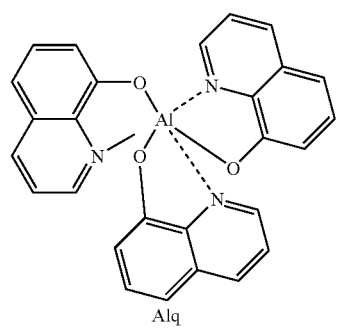
Alq

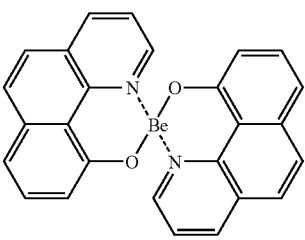
BeBq

The electron-injection transporting material may be arbitrarily selected from materials which facilitate injection of an electron from a cathode and which have a function of transporting the injected electron into a light emission layer. The material is selected in consideration of, for example, the balance with the mobility of a carrier of the hole transport material. Examples of a material having electron-injection transporting property include, but are not limited to, an oxadiazole derivative, an oxazole derivative, a thiazole derivative, a thiadiazole derivative, a pyrazine derivative, a triazole derivative, a triazine derivative, a perylene derivative, a quinoline derivative, a quinoxaline derivative, a fluorenone derivative, an anthrone derivative, a phenanthroline derivative, and an organometallic complex. Specific examples thereof will be partly shown below.

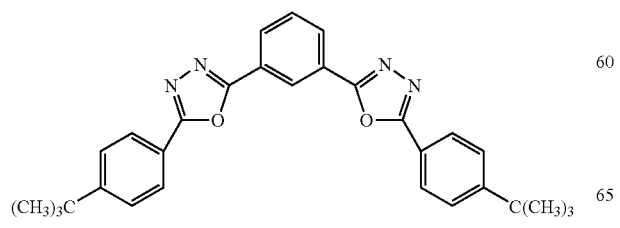

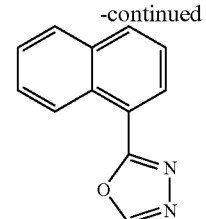
-continued

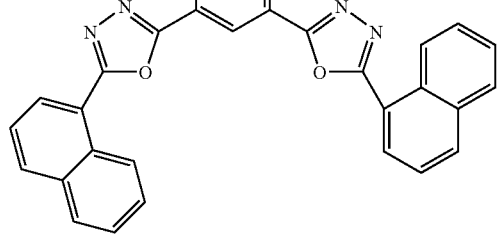

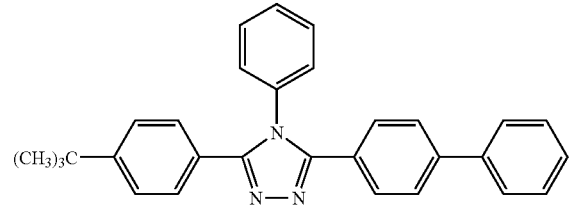
TAZ

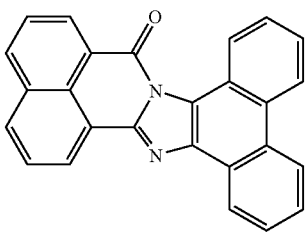

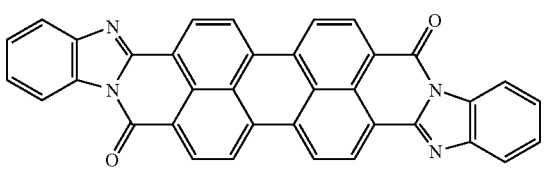

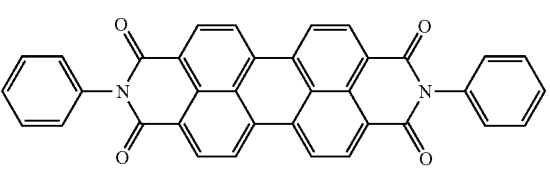

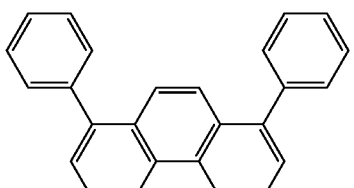
Bphen

-continued

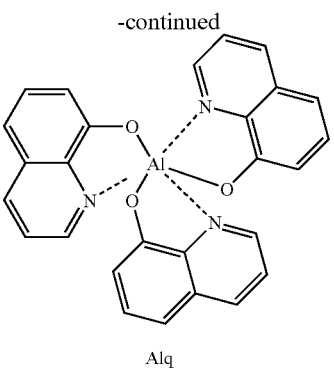

Alq

In the organic light-emitting device according to the present invention, the layer containing the pyrene compound of the present invention and layers containing other organic compounds are each formed through the following method. A thin film is generally formed through a vacuum deposition method, an ionized deposition method, sputtering, plasma, or a known coating method (such as a spin coating, dipping, casting, LB, or inkjet method) in which a compound is dissolved in an appropriate solvent. In film formation through a coating method, in particular, a film may be formed by using a compound in combination with an appropriate binder resin.

The binder resin may be selected from a wide variety of binder resins. Examples of the binder resin include, but are not limited to: a polyvinyl carbazole resin; a polycarbonate resin; a polyester resin; a polyallylate resin; a polystyrene resin; an ABS resin; a polybutadine resin; a polyurethane resin; an acrylic resin; a methacrylic resin; a butyral resin; a polyvinyl acetal resin; a polyamide resin; a polyimide resin; a polyethylene resin; a polyethersulfone resin; a diallyl phthalate resin; a phenol resin; an epoxy resin; a silicone resin; a polysulfone resin; and a urea resin. One kind of binder resin may be used alone, or two or more kinds thereof may be mixed and used as a copolymer. Further, an additive such as a known plasticizer, antioxidant, or ultraviolet absorber may be used in combination as required.

An anode material preferably has as large a work function as possible, and examples thereof include: a metal element such as gold, platinum, silver, copper, nickel, palladium, cobalt, selenium, vanadium, or tungsten; an alloy thereof; and a metal oxide such as tin oxide, zinc oxide, indium oxide, indium tin oxide (ITO), or indium zinc oxide. Further, a conductive polymer such as polyaniline, polypyrrole, polythiophene, or polyphenylene sulfide may also be used. Each of those electrode materials may be used alone, or two or more kinds thereof may be used in combination. Further, the anode may have a single layer structure or a multilayer structure.

Meanwhile, a cathode material preferably has as small a work function as possible, and examples thereof include: a metal element such as lithium, sodium, potassium, calcium, magnesium, aluminum, indium, ruthenium, titanium, manganese, yttrium, silver, lead, tin, or chromium; and an alloy thereof such as a lithium-indium alloy, a sodium-potassium alloy, a magnesium-silver alloy, an aluminum-lithium alloy, an aluminum-magnesium alloy, or a magnesium-indium alloy. A metal oxide such as indium tin oxide (ITO) may also be used. Each of those electrode materials may be used alone, or two or more kinds thereof may be used in combination. Further, the cathode may have a single layer structure or a multilayer structure.

The substrate to be used in the present invention is not particularly limited, but examples thereof include: an opaque substrate such as a metallic substrate or a ceramics substrate; and a transparent substrate such as a glass substrate, a quartz substrate, or a plastic sheet substrate. In addition, the substrate may have a color filter film, a fluorescent color converting filter film, a dielectric reflection film, or the like for controlling luminescent color.

Further, a protective layer or a sealing layer may be formed on the produced device to prevent contact between the device and oxygen, moisture, or the like. Examples of the protective layer include: a diamond thin film; a film formed of an inorganic material such as metal oxide or metal nitride; a polymer film formed of a fluorine resin, polyparaxylene, polyethylene, a silicone resin, a polystyrene resin, or the like; and a photocurable resin. Further, the device itself may be covered with glass, an airtight film, a metal, or the like and packaged with an appropriate sealing resin.

A thin film transistor (TFT) may be produced on a substrate, and then the device of the present invention may be produced to be connected to TFT.

Regarding the emission direction of a device, the device may have a bottom emission structure (structure in which light is emitted from a substrate side) or a top emission structure (structure in which light is emitted from an opposite side of the substrate).

Hereinafter, the present invention will be described more specifically with reference to examples, but the present invention is not limited to the examples.

Example 1

Method of Producing Exemplified Compound No. 3

(1) Synthesis of Intermediate (9-bromo-10-(1-pyrenyl)anthracene))

In a stream of nitrogen, 16.8 g (50 mmol) of 9,10-dibromoanthracene was dissolved in a deaerated mixed solvent containing 300 ml of toluene and 200 ml of ethanol, and the whole was stirred. Then, an aqueous solution of sodium carbonate prepared by dissolving 10.6 g of anhydrous sodium carbonate in 100 ml of water was added to the mixture, and 5.78 g (5 mmol) of tetrakis(triphenylphosphine)palladium was added thereto. The resulting solution was stirred in an oil bath heated to 50° C. 16.4 g (50 mmol) of 1-[4,4,5,5-tetramethyl-1,3,2-dioxaboranyl]pyrene dissolved in 100 ml of toluene was added dropwise to the solution. In a stream of nitrogen, the resulting mixture was stirred under heating for about 4 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 20.6 g of 9-bromo-10-(1-pyrenyl)anthracene.

(2) Synthesis of Exemplified Compound No. 3

In a nitrogen atmosphere, 344 mg (1.53 mmol) of palladium acetate and 1.86 g (6.12 mmol) of tri-o-tolylphosphine were dissolved in 300 ml of xylene, and the whole was stirred at room temperature for 15 minutes. After addition of 100 ml of xylene, 10 g (21.9 mmol) of 9-bromo-10-(1-pyrenyl)anthracene was added to the mixture, and the whole was stirred for 5 minutes in an oil bath heated to 50° C. 4.39 g (26 mmol) of N,N-diphenylamine was dissolved in 30 ml of xylene, and the resulting solution was added dropwise into the mixture. Subsequently, 4.63 g (48.2 mmol) of sodium tert-butoxide was added to the mixture. The mixture was stirred under heating for about 5 hours in an oil bath heated to 130° C. The temperature of the reaction solution was returned to room temperature, and 100 ml of water was added to the reaction solution, to thereby separate a water layer and an organic layer. Then, the water layer was extracted with toluene and ethyl acetate and dried together with the organic layer by using sodium sulfate. The solvent was distilled off, and the residue was purified by silica gel column chromatography (toluene:heptane=1:3), to thereby obtain 8.7 g of Exemplified Compound No. 3.

Examples 2 to 6

Methods of Producing Exemplified Compounds Nos. 1, 2, 6, 7, and 8

The following compounds were used instead of N,N-diphenylamine. That is, Exemplified Compounds Nos. 1, 2, 6, 7, and 8 were produced in the same manner as in Example 1 except that N-(2-naphthyl)-N-phenylamine, N-(1-naphthyl)-N-phenylamine, N-(9-phenanthryl)-N-phenylamine, N-(9-anthryl)-N-phenylamine, and N-(1-pyrenyl)-N-phenylamine were used respectively.

Example 7

Method of Producing Exemplified Compound No. 5

(1) Synthesis of Intermediate (9-[N,N-bis(4-methylphenyl)amino]-10-bromoanthracene)

In a stream of nitrogen, 11.2 g (30 mmol) of 9-[N,N-bis(4-methylphenyl)amino]anthracene was dissolved in 100 ml of dioxane, and the whole was stirred at room temperature. Then, 1.68 g (30 mmol) of potassium hydroxide dissolved in 3 ml of water was added to the mixture dropwise. 5.75 g of bromine was added thereto, and the whole was stirred for 30 minutes. A 5% aqueous solution of sodium thiosulfate was added to the mixture, and the whole was stirred for 1 hour. The product was filtrated and washed with methanol. The product was recrystallized by using toluene, to thereby obtain 11.3 g of 9-[N,N-bis(4-methylphenyl)amino]-10-bromoanthracene.

(2) Synthesis of Exemplified Compound No. 5

In a stream of nitrogen, the following compounds were dissolved in a deaerated mixed solvent containing 80 ml of toluene and 40 ml of ethanol, and the whole was stirred. That is, 2.5 g (6.7 mmol) of 9-[N,N-bis(4-methylphenyl)amino]-10-bromoanthracene and 2.75 g (8.38 mmol) of 1-(4,4,5,5-tetramethyl-1,3,2-dioxaboranyl)pyrene were used. Then, an aqueous solution of sodium carbonate prepared by dissolving 850 mg of anhydrous sodium carbonate in 20 ml of water was added dropwise to the mixture. In a stream of nitrogen, the mixture was stirred under heating for 1 hour in an oil bath heated to 50° C., and 770 mg (0.67 mmol) of tetrakis(triphenylphosphine)palladium was added thereto. The resulting solution was stirred under heating for about 4 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 22 g of Exemplified Compound No. 5.

Example 8

Method of Producing Exemplified Compound No. 4

18 g of Exemplified Compound No. 4 was produced in the same manner and on the same scale as those of Example 7 by using 13.7 g (30 mmol) of 9-[N,N-bis(4-tert-butylphenyl)amino]anthracene.

Examples 9 to 11

Methods of Producing Exemplified Compounds Nos. 12, 19, and 24

Exemplified Compounds Nos. 12, 19, and 24 were produced in the same manner and under the same synthesis conditions as those of Example 7 through a reaction between 9-[N,N-bis(4-methylphenyl)amino]-10-bromoanthracene and the following compounds.
That is, Exemplified Compound No. 12 was produced by using 4,4,5,5-tetramethyl-1,3,2-dioxaborane derived from 1-bromo-7-tert-butyl-3-methylpyrene (synthesized in accordance with Organic Preparations and Procedures International (1997), 29, 321-330).
Exemplified Compound No. 19 was produced by using 4,4,5,5-tetramethyl-1,3,2-dioxaborane derived from 1-bromopyrene-d9.
Exemplified Compound No. 24 was produced by using 4,4,5,5-tetramethyl-1,3,2-dioxaborane derived from 2-bromopyrene.

Example 12

Method of Producing Exemplified No. 95

2.1 g of Exemplified Compound No. 95 was produced in the same manner and under the same synthesis conditions as those of Example 7.
2.1 g of Exemplified Compound No. 95 was produced through a reaction between: 2 g (3.73 mmol) of 9-[N,N-bis(4-tert-butylphenyl)amino]-10-bromoanthracene; and 1.8 g (4.52 mmol) of 4,4,5,5-tetramethyl-1,3,2-dioxaborane derived from 1-bromo-7-tert-butyl-3-methylpyrene.
4,4,5,5-tetramethyl-1,3,2-dioxaborane can be obtained from 1-bromo-7-tert-butyl-3-methylpyrene.
Exemplified Compound No. 95 can be obtained through a reaction between 2 g (3.73 mmol) of the former compound and 1.8 g (4.52 mmol) of the latter compound.

Example 13

Method of Producing Exemplified Compound No. 14

10 g (21.9 mmol) of 9-bromo-10-(1-pyrenyl)anthracene was synthesized in the same manner as in Example 1.
14.5 g (32.9 mmol) of 1-[N-(4-methylphenyl)-N-(4-tert-butylphenyl)amino]-4-[4,4,5,5-tetramethyl-1,3,2-dioxaboranyl]benzene was prepared.
In a stream of nitrogen, both compounds were dissolved in a deaerated mixed solvent containing 200 ml of toluene and 100 ml of ethanol, and the whole was stirred.
Then, an aqueous solution of sodium carbonate prepared by dissolving 5.2 g of anhydrous sodium carbonate in 50 ml of water was added to the mixture. The resulting solution was stirred in an oil bath heated to 50° C., and 2.66 g (2.30 mmol) of tetrakis(triphenylphosphine)palladium was added thereto. The resulting solution was stirred under heating for about 5 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 11 g of Exemplified Compound No. 14.

Example 14

Method of Producing Exemplified Compound No. 56

(1) Synthesis of Intermediate (3-bromo-5-[9-(N,N-bis(4-methylphenyl)amino)-10-anthryl]toluene)

In a stream of nitrogen, 12.5 g (50 mmol) of 3,5-dibromotoluene was dissolved in a deaerated mixed solvent containing 300 ml of toluene and 200 ml of ethanol, and the whole was stirred.

Then, an aqueous solution of sodium carbonate prepared by dissolving 10.6 g of anhydrous sodium carbonate in 100 ml of water was added to the mixture, and 5.78 g (5 mmol) of tetrakis(triphenylphosphine)palladium was added thereto. The resulting solution was stirred in an oil bath heated to 50° C., and 20.9 g (50 mmol) of 9-(N,N-bis(4-methylphenyl)amino)anthryl-10-boronic acid dissolved in 100 ml of toluene was added dropwise slowly into the solution. In a stream of nitrogen, the resulting solution was stirred under heating for about 4 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 16.8 g of 3-bromo-5-[9-(N,N-bis(4-methylphenyl)amino)-10-anthryl]toluene.

(2) Synthesis of Exemplified Compound No. 56

2.5 g (4.61 mmol) of 3-bromo-5-[9-(N,N-bis(4-methylphenyl)amino)-10-anthryl]toluene was prepared.

Then, 1.89 g (5.76 mmol) of 1-(4,4,5,5-tetramethyl-1,3,2-dioxaboranyl)pyrene was prepared.

In a stream of nitrogen, both compounds were dissolved in a deaerated mixed solvent containing 80 ml of toluene and 40 ml of ethanol, and the whole was stirred. Then, an aqueous solution of sodium carbonate prepared by dissolving 916 mg of anhydrous sodium carbonate in 20 ml of water was added dropwise to the mixture. In a stream of nitrogen, the mixture was stirred for 1 hour in an oil bath heated to 50° C., and 533 mg (0.461 mmol) of tetrakis(triphenylphosphine)palladium was added thereto. The resulting solution was stirred under heating for about 4 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 2.91 g of Exemplified Compound No. 56.

Examples 15 to 18

Methods of Producing Exemplified Compounds Nos. 69, 71, 75, and 78

Exemplified Compounds Nos. 69, 71, 75, and 78 were produced in the same manner and under the same synthesis conditions as those of Example 14 by using the following compounds instead of 1-(4,4,5,5-tetramethyl-1,3,2-dioxaboranyl)pyrene.

That is, Exemplified Compound No. 69 was produced by using 1-(4,4,5,5-tetramethyl-1,3,2-dioxaboranyl)pyrene-d9 derived from 1-bromopyrene-d9 (exemplified in Example 10).

Exemplified Compound No. 71 was produced by using 2-(4,4,5,5-tetramethyl-1,3,2-dioxaboranyl)pyrene derived from 2-bromopyrene (exemplified in Example 11).

Exemplified Compound No. 75 was produced by using 1-(4,4,5,5-tetramethyl-1,3,2-dioxaboranyl)-7-tert-butyl-3-methoxypyrene derived from 1-bromo-7-tert-butyl-3-methoxypyrene (synthesized in accordance with Organic Preparations and Procedures International (1997), 29, 321-330).

Exemplified Compound No. 78 was produced by using 1-(4,4,5,5-tetramethyl-1,3,2-dioxaboranyl)-7-tert-butyl-3-methylpyrene shown in Example 9.

Example 19

Method of Producing Exemplified Compound No. 57

3,5-dibromo-tert-butylbenzene was synthesized by using 4-tert-butylaniline in accordance with a document (J. Am. Chem. Soc. (1991), 113, 4238). Exemplified Compound No. 57 was produced in the same manner and under the same synthesis conditions as those of Example 13 by using 3,5-dibromo-tert-butylbenzene instead of 3,5-dibromotoluene.

Example 20

Method of Producing Exemplified Compound No. 77

(1) Synthesis of Intermediate (3-bromo-5-(1-pyrenyl)toluene)

3-bromo-5-(1-pyrenyl)toluene was synthesized under the same conditions as those of Example 1. In a stream of nitrogen, 12.5 g (50 mmol) of 3,5-dibromotoluene was dissolved in a deaerated mixed solvent containing 300 ml of toluene and 200 ml of ethanol, and the whole was stirred. Then, an aqueous solution of sodium carbonate prepared by dissolving 10.6 g of anhydrous sodium carbonate in 100 ml of water was added to the mixture. Then, 5.78 g (5 mmol) of tetrakis(triphenylphosphine)palladium was added thereto. The resulting solution was stirred in an oil bath heated to 50° C. Then, 16.4 g (50 mmol) of 1-[4,4,5,5-tetramethyl-1,3,2-dioxaboranyl]pyrene dissolved in 100 ml of toluene was added dropwise slowly to the solution in three separate portions. In a stream of nitrogen, the resulting solution was stirred under heating for about 4 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 10.2 g of 3-bromo-5-(1-pyrenyl)toluene.

(2) Synthesis of Exemplified Compound No. 77

9.51 g (21.9 mmol) of 3-(1-pyrenyl)-5-(4,4,5,5-tetramethyl-1,3,2-dioxaboranyl)-toluene was obtained from 3-bromo-5-(1-pyrenyl)toluene. 17.4 g (32.9 mmol) of 9-bromo-10-{4-[N,N-bis(4-methylphenyl)amino]phenyl}anthracene was prepared. In a stream of nitrogen, both compounds were dissolved in a deaerated mixed solvent containing 200 ml of toluene and 100 ml of ethanol, and the whole was stirred. Then, an aqueous solution of sodium carbonate prepared by dissolving 5.2 g of anhydrous sodium carbonate in 50 ml of water was added to the mixture. The solution was stirred in an oil bath heated to 50° C., and 2.66 g (2.30 mmol) of tetrakis(triphenylphosphine)palladium was added thereto. The resulting solution was stirred under heating for about 5 hours in an oil bath heated to 80° C. The temperature of the reaction solution was returned to room temperature, and an organic layer was separated by adding toluene, ethyl acetate, and water. The organic layer was dried by using magnesium sulfate to distill off the solvent. The resultant was purified by silica gel column chromatography (toluene:heptane=1:3), to thereby obtain 11 g of Exemplified Compound No. 77.

Example 21

An organic light-emitting device having the structure shown in FIG. 3 was produced through the method described below.

Indium tin oxide (ITO) as the anode 2 was formed as a film having a thickness of 120 nm on a glass substrate as the substrate 1 through a sputtering method, and the resultant was used as a transparent conductive supporting substrate. The resulting substrate was subjected to ultrasonic cleaning in acetone and isopropyl alcohol (IPA) in the order given. Then, the substrate was washed in boiling IPA and dried. The substrate was subjected to UV/ozone cleaning to be used as a transparent conductive supporting substrate.

A chloroform solution containing 0.2 wt % of a compound represented by the following structural formula as a hole transport material was prepared.

This solution was dropped onto the above-mentioned ITO electrode and formed into a film on the ITO electrode through spin coating at a revolving speed of 500 rpm for 10 seconds at first and then at a revolving speed of 1,000 rpm for 1 minute. Then, the whole was placed in a vacuum oven at 80° C. and dried for 10 minutes, to thereby completely remove the solvent in the thin film. The thus-formed hole transport layer 5 had a thickness of 25 nm.

Next, as the light emission layer 3, Exemplified Compound No. 3 described above was deposited on the hole transport layer 5. The resulting light emission layer 3 had a thickness of 20 nm. A degree of vacuum during deposition was $1.0 \times 10^{-4}$ Pa and a film formation rate was 0.2 to 0.3 nm/second.

Further, as the electron transport layer 6, bathophenanthroline (BPhen) was formed into a film having a thickness of 50 nm through a vacuum deposition method. A degree of vacuum during deposition was $1.0 \times 10^{-4}$ Pa and a film formation rate was 0.2 to 0.3 nm/second.

Next, lithium fluoride (LiF) was formed into a film having a thickness of 0.5 nm on the organic layer described above through a vacuum deposition method, and an aluminum film having a thickness of 150 nm was formed thereon through a vacuum deposition method, to thereby produce an electron-injection electrode (cathode 4). As a result, an organic light-emitting device with the electron-injection electrode (cathode 4) was produced. A degree of vacuum during deposition was $1.0 \times 10^{-4}$ Pa. A lithium fluoride film formation rate was 0.05 nm/second, and an aluminum film formation rate was 1.0 to 1.2 nm/second.

The obtained organic EL device was covered with a protective glass and sealed with an acrylic resin binder in a dry air atmosphere to prevent degradation of the device by adsorption of moisture thereon.

Under application of a voltage of 4 V to the thus-obtained device having the ITO electrode (anode 2) as a positive electrode and the Al electrode (cathode 4) as a negative electrode, green light emission with an emission luminance of 960 cd/m$^2$ and a luminous efficiency of 7.6 lm/W was observed.

Further, the voltage was applied to the device for 100 hours while a current density was maintained at 3.0 mA/cm$^2$ in a nitrogen atmosphere, resulting in slight luminance degradation from an initial luminance of 290 cd/m$^2$ to a luminance of 275 cd/m$^2$ after 100 hours.

Comparative Example 1

An organic light-emitting device was produced in the same manner as in Example 21 and was subjected to the same evaluation except that the following comparative compound was used instead of Exemplified Compound No. 3.

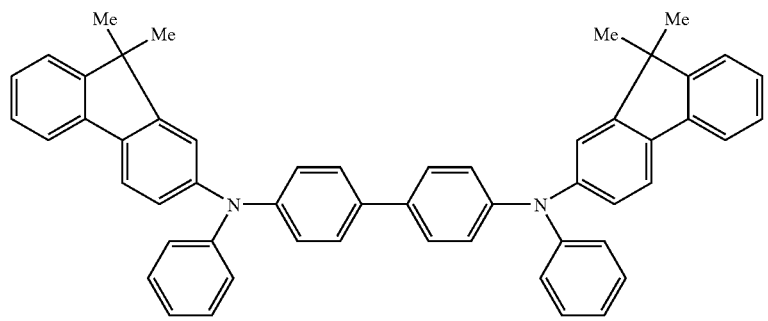

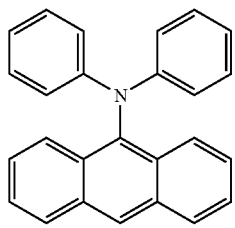

Under application of a voltage of 4 V, green light emission with an emission luminance of 190 cd/m² and a luminous efficiency of 2 lm/W was observed. Further, the voltage was applied to the device for 100 hours while a current density was maintained at 3.0 mA/cm² in a nitrogen atmosphere, resulting in extensive luminance degradation from an initial luminance of 52 cd/m² to a luminance of 26 cd/m² after 100 hours.

Examples 22 to 25

Organic light-emitting devices were produced in the same manner as in Example 21 and were subjected to the same evaluation except that the compounds shown in Table 1 were used instead of Exemplified Compound No. 3. Table 1 shows the results.

TABLE 1

| Example | Exemplified Compound No. | Applied voltage (V) | Luminance (cd/m²) | Efficiency (1 m/W) |
|---|---|---|---|---|
| 22 | 2 | 4.0 | 910 | 7.1 |
| 23 | 19 | 4.0 | 1020 | 8.0 |
| 24 | 24 | 4.0 | 780 | 7.7 |
| 25 | 55 | 4.0 | 1270 | 10 |

Example 26

An organic light-emitting device was produced in the same manner as in Example 21 except that 2,9-bis[2-(9,9-dimethylfluorenyl)]phenanthroline was used for the electron transport layer 6 and Exemplified Compound No. 5 was used for the light emission layer 3.

Under application of a voltage of 4 V to the thus-obtained device having the ITO electrode (anode 2) as a positive electrode and the Al electrode (cathode 4) as a negative electrode, green light emission with an emission luminance of 970 cd/m² and a luminous efficiency of 7.7 lm/W was observed.

Examples 27 to 45

Organic light-emitting devices were produced in the same manner as in Example 26 and were subjected to the same evaluation except that the compounds shown in Table 2 were used instead of Exemplified Compound No. 5. Table 2 shows the results.

The voltage was applied to the device produced in each of Examples 28, 33, 39, and 44 for 100 hours while a current density was maintained at 3.0 mA/cm² in a nitrogen atmosphere, resulting in slight luminance degradation: from an initial luminance of 290 cd/m² to a luminance of 280 cd/m² after 100 hours in Example 28; from an initial luminance of 410 cd/m² to a luminance of 390 cd/m² after 100 hours in Example 33; from an initial luminance of 650 cd/m² to a luminance of 635 cd/m² after 100 hours in Example 39; and from an initial luminance of 590 cd/m² to a luminance of 570 cd/m² after 100 hours in Example 44.

TABLE 2

| Example | Exemplified Compound No. | Applied voltage (V) | Luminance (cd/m²) | Efficiency (1 m/W) |
|---|---|---|---|---|
| 27 | 4 | 4.0 | 770 | 7.6 |
| 28 | 12 | 4.0 | 590 | 7.7 |
| 29 | 14 | 4.0 | 330 | 3.3 |
| 30 | 36 | 4.0 | 780 | 7.7 |
| 31 | 47 | 4.0 | 750 | 5.9 |
| 32 | 49 | 4.0 | 970 | 7.7 |
| 33 | 56 | 4.0 | 1360 | 10.7 |
| 34 | 57 | 4.0 | 1090 | 10.7 |
| 35 | 71 | 4.0 | 940 | 9.2 |
| 36 | 77 | 4.0 | 350 | 3.4 |
| 37 | 78 | 4.0 | 1100 | 10.8 |
| 38 | 91 | 4.0 | 1080 | 10.7 |
| 39 | 95 | 4.0 | 1350 | 11.2 |
| 40 | 96 | 4.0 | 1040 | 10.2 |
| 41 | 98 | 4.0 | 210 | 2.4 |
| 42 | 99 | 4.0 | 170 | 2.2 |
| 43 | 100 | 4.0 | 170 | 1.9 |
| 44 | 105 | 4.0 | 1180 | 11.0 |
| 45 | 107 | 4.0 | 1240 | 10.5 |

Comparative Example 2

An organic light-emitting device was produced in the same manner as in Example 26 and was subjected to the same evaluation except that the following comparative compound was used instead of Exemplified Compound No. 5.

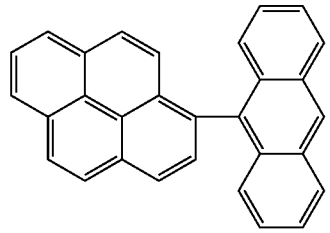

Under application of a voltage of 4 V, blue light emission with an emission luminance of 50 cd/m² and a luminous efficiency of 0.3 lm/W was observed. Further, the voltage was applied to the device for 100 hours while a current density was maintained at 10 mA/cm² in a nitrogen atmosphere, resulting in extensive luminance degradation from an initial luminance of 37 cd/m² to a luminance of 16 cd/m² after 100 hours.

This application claims priority from Japanese Patent Application No. 2004-342463 filed on Nov. 26, 2004 and Japanese Patent Application No. 2005-273622 filed Sep. 21, 2005, which are hereby incorporated by reference herein.

What is claimed is:

1. An aminoanthryl derivative-substituted pyrene compound represented by the following general formula:

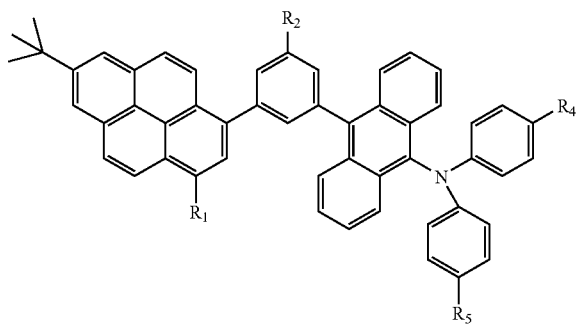

wherein $R_1$, $R_4$, and $R_5$ each independently represent a substituted or unsubstituted alkyl group; and $R_2$ represents a group selected from the group consisting of a hydrogen atom and a substituted or unsubstituted alkyl group.

2. The aminoanthryl derivative-substituted pyrene compound according to claim 1, which is represented by the following general formula:

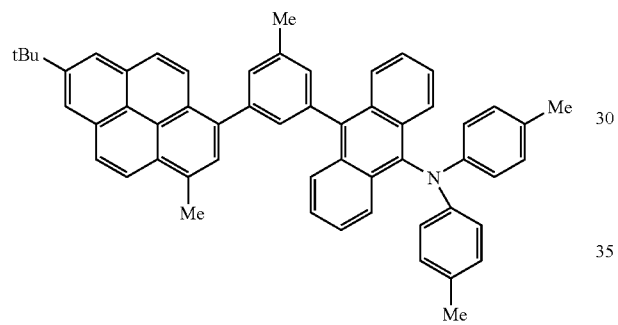

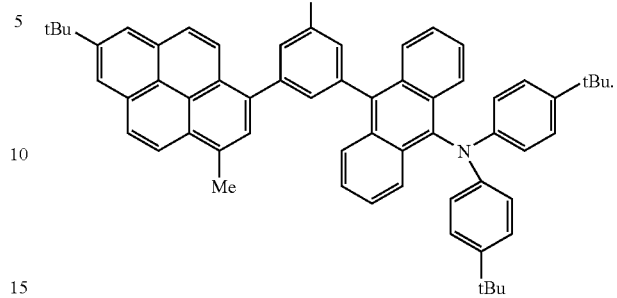

3. An organic blue light-emitting device comprising:

a pair of electrodes consisting of an anode and a cathode in which at least one electrode is transparent or translucent; and a layer or a plurality of layers each containing an organic compound and spaced between the pair of electrodes, wherein at least one of the layers each containing an organic compound contains at least one aminoanthryl derivative-substituted pyrene compound according to claim 1.

4. The organic light-emitting device according to claim 3, wherein the layer containing at least one aminoanthryl derivative-substituted pyrene compound comprises a light emission layer.

* * * * *